(12) United States Patent
Kopke et al.

(10) Patent No.: US 6,649,621 B2
(45) Date of Patent: *Nov. 18, 2003

(54) PREVENTION OR REVERSAL OF SENSORINEURAL HEARING LOSS (SNHL) THROUGH BIOLOGIC MECHANISMS

(75) Inventors: Richard D. Kopke, San Diego, CA (US); Donald Henderson, Clarence, NY (US); Michael E. Hoffer, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/766,625

(22) Filed: Jan. 23, 2001

(65) Prior Publication Data

US 2001/0007871 A1 Jul. 12, 2001

Related U.S. Application Data

(63) Continuation-in-part of application No. 09/126,707, filed on Jul. 31, 1998, now Pat. No. 6,177,434
(60) Provisional application No. 60/069,761, filed on Dec. 16, 1997.

(51) Int. Cl.[7] .................... A61K 31/517; A61K 31/425; A61K 31/205; A61K 31/255

(52) U.S. Cl. .................... 514/266.1; 514/369; 514/562; 514/547; 514/956; 514/517

(58) Field of Search .................... 514/266, 369, 514/562, 547, 956

(56) References Cited

U.S. PATENT DOCUMENTS

| | | | | |
|---|---|---|---|---|
| 3,422,186 A | * | 1/1969 | Sasmor | 424/79 |
| 5,977,162 A | * | 11/1999 | Seidman | 514/440 |
| 6,066,652 A | * | 5/2000 | Zenner et al. | 514/317 |
| 6,093,417 A | * | 7/2000 | Petrus | 424/437 |
| 6,177,434 B1 | * | 1/2001 | Kopke et al. | 514/266 |

* cited by examiner

*Primary Examiner*—Frederick Krass
*Assistant Examiner*—Donna Jagoe
(74) *Attorney, Agent, or Firm*—Philip E. Ketner; Joseph K. Hemby, Jr.; Barry Edelberg

(57) ABSTRACT

The invention presents methods for preventing and treating sensorineural hearing loss and is directed to the restoration or protection of hair cells in individuals experiencing a non-presbycusis type sensorineural hearing loss or who are at risk for an acute hearing loss due to exposure to noise, toxins, or other stressors. More specifically, the present invention relates to the use of agents which augment inner ear antioxidant defenses (e.g. acetyl-L-carnitine, steroids, compounds that are transported into inner ear hair cells and then synthesized by said cells into glutahione) to prevent and/or reverse hearing loss induced by noise, toxins, or other stressors.

8 Claims, 14 Drawing Sheets

PREVENTION OR REVERSAL OF SENSORINEURAL HEARING LOSS (SNHL) THROUGH BIOLOGIC MECHANISMS

RELATED APPLICATIONS

This application is a continuation-in-part and divisional of U.S. patent application Ser. No. 09/126,707, filed Jul. 31, 1998 (the entirety of which is incorporated herein by reference for all purposes), which claims benefit of Provisional Application Ser. 60/069,761, filed Dec. 16, 1997.

BACKGROUND OF THE INVENTION

1. Field of the Invention

This invention relates to a method and composition for preventing and/or reversing sensorineural hearing loss (SNHL) or toxin-induced hearing loss. More specifically, this invention relates to the use of agents which augment inner ear antioxidant defenses such as adenosine agonists or up-regulating agents and/or agents which increase inner ear glutathione levels to prevent and/or reverse hearing loss induced by noise or toxin. In addition, this invention covers agents that curtail activated programmed cell death pathways and induce/enhance cell repair mechanisms in the inner ear.

2. Description of the Prior Art

SNHL is a very common problem for service members and civilian government employees. Approximately 450 million dollars is spent annually to compensate service members for hearing loss (1). Despite hearing conservation programs, 20–30% of service members develop compensable hearing loss after 10 years in the service (2). The sense of hearing is critical for combat and operational readiness of soldiers and sailors. Both temporary and permanent hearing threshold impairments decrease the ability to communicate and to detect enemy movements (3). Successful implementation of medical treatment to prevent or reverse SNHL as an augmentation to established hearing conservation programs has the potential to save millions of dollars annually and to significantly improve operational readiness.

It is established by the Center for Disease Control that approximately 30 million people in the U.S suffer from SNHL (4). The potential for commercialization is very extensive and would include workers in factories, construction operations, communications, and the airline industry to name a few. Many people working in an environment with damaging noise or toxins would potentially benefit from this treatment. In addition, individuals receiving toxic medications for other forms of therapy (i.e. cancer chemotherapy) can suffer SNHL. An idiopathic form of SNHL also exists.

Currently there are no published effective topical medications to prevent or reverse SNHL. There are no published reports of topical, oral, or systemic medications to treat noise-induced hearing loss (NIHL). This invention differs from mechanical noise attenuators or hearing protection devices in that it does not need to be worn and does not decrease hearing acuity as hearing protectors do. Also, this treatment has the potential to reverse SNHL after it is occurred.

Additionally, cisplatin and aminoglycoside antibiotics such as gentamicin represent useful commonly prescribed therapeutic agents which are toxic to the ear and cause sensorineural hearing loss (6,7,15). Gentamicin is used as an agent delivered indirectly to the inner ear via the middle crossing the round window membrane to destroy balance function in an inner ear affected by Meniere's disease (28). One of the limitations of this therapy is that the auditory portion of the inner ear is also often damaged leading to sensorineural hearing loss (29). Thus there is a need to selectively protect the auditory hair cells while eliminating inner ear balance function with the gentamicin.

SUMMARY OF THE INVENTION

Accordingly, an object of this invention is to prevent sensorineural hearing loss and sensorineural hearing loss caused by noise.

A further object of this invention is to reverse sensorineural hearing loss and sensorineural hearing loss induced by noise.

Yet another object of the invention is to prevent and or reverse hearing loss by the topical application of a compound or combination of compounds which increase inner ear glutathione (GSH) levels and/or augment other inner ear antioxidant defenses, and agents that curtail activated programmed cell death pathways and/or induce/enhance cell repair mechanisms in the inner ear.

Another object of the invention is to protect auditory hair cells from toxic injury by cisplatin or gentamicin.

These and additional objects of the invention are accomplished by preventing and/or reversing inner ear damage due to noise or toxins by upregulating antioxidant enzyme activity by applying agents such as R-N6 Phenylisopropyl adenosine (R-PIA) to the round window membrane of the inner ear or systemically, and/or by also applying agents such as 1–2-oxothiazolidine-4-carboxylic acid (Procysteine) to the round window membrane or by giving it systemically. Selective auditory hair cell protection in the face of gentamicin exposure by concomitant delivery of an NMDA antagonist or glial dervied neurotrophic factor (GDNF) with the gentamicin. These and additional agents are also accomplished by curtailing activated programmed cell death pathways and/or inducing/enhancing cell repair mechanisms in the inner ear. One particularly interesting combination of agents is a mixture of L-N-acetylcysteine (L-NAC) and an ester or salt of salicylic acid. Both agents may be administered orally, which is a desirable characteristic. Low dose salicylate is known to scavenge hydroxyl free radicals (Ohiemiller, In vivo measurement of cochlear reactive oxygen species (ROS) in mice: effects of noise exposure and cochi ear ischemia., Twenty-first Midwinter Research Meeting of the Association for Research in Otolaryngology Association for Research in Otolaryngology, St. Petersburg Beach, Fla., pp. 130, abstract 518 (1998)) and in so doing to form the iron chelator dihydroxybenzoate (DHB). Iron chelators can prevent ROS formation by inhibiting the Fenton reaction (Yamasoba et al., Protection from noise-induced coch/ear damage by iron chelators, Twenty-first Midwinter Research Meeting of the Association for Research in Otolaryngology Association for Research in Otolaryngology, St. Petersburg Beach, Fla., pp. 133, abstract 531 (1998)). Salicylate may also inhibit NF-κB, a potential activator of inflammatory or cell death pathways (Kopp and Ghosh, "Inhibition of NE-k B by sodium salicylate and aspirin" (see comments), *Science*, 265, 956–959 1994; Yin et al., The anti-inflammatory agents aspirin and salicylate inhibit the activity of IκB kinase-β, *Nature*, 396, 77–80 (1998)) or induce heat shock proteins which are known to provide a protective effect for the cochlea (Altschuler et al., In *Auditory Plasticity and Regeneration*, (Eds, Salvi R. J., H. D., Fiorini F., & Colletti V.) Tieman Medical Publications, New York 1996). L-NAC is another potentially effective candidate because it acts as an ROS scavenger as well as a neuroprotective agent, by increasing intracellular GSH. L-NAC is a well-tolerated antidote to ROS-induced liver damage due to acetaminophen overdose (Kopke et al., Am J Otol, 18,559–571 1997). GSH ester applied to the round window membrane of chinchillas substantially prevents noise-induced hair cell loss (Hight et al., *Midwinter Meeting of the Association for Research in Otolaryngology*, Vol. 22, Abstract 602 St. Petersburg Beach, Fla. (1999)). Also, alpha lipoic acid, D-methionine, and acetyl-L-carnitine, administered either alone or in combination with one or more of the other protective agents described herein, either orally, or through an inner ear catheter, can provide a protective and/or restorative effect (after sudden hearing loss has occurred) for the cochlea. Additionally, the combination of these agents with L-NAC should be more effective than either alpha lipoic acid, D-methionine, or acetyl-L-carnitine alone.

The agent(s) may be applied before, during or after the noise trauma or toxin exposure. Currently there is no published effective topical medication to prevent or reverse SNHL, no published effective medication to prevent or reverse NIHL, and no published medical therapy to selectively protect auditory hair cells from gentamicin toxicity. This invention differs from mechanical noise attenuators or hearing protection devices in that it does not need to be worn and does not decrease hearing acuity as hearing protectors do. Also, this treatment has the potential to reverse SNHL or toxic hearing loss after it is occurred.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures are diagrammatic and no attempt is made to indicate actual scales or precise ratios. Proportional relationships are shown as approximations.

FIG. 13A demonstrates that there is very little inner or outer hair cell loss in non-noise exposed animals. FIG. 13B shows that the six hour 4 kHz octave band noise exposure at 105 dB SPL in untreated saline-noise animals caused substantial hair cell loss, with a maximal loss occurring at 5 to 6 kHz. Sixty to 80% of the outer hair cells were lost in the region between 3 and 8 kHz. Fewer inner hair cells were lost (maximum of 30%) in approximately the same region of the cochlea. FIG. 13C shows there was a substantial reduction in both outer and inner hair cell loss in the pre-treatment group compared to the saline-noise group (20 to 30% outer hair cell loss versus 60 to 80%, 0 to 10% inner hair cell loss versus 20 to 30%; three weeks post noise exposure). FIG. 13D shows there was no difference in hair cell loss in the post-treatment group compared to the saline-noise group.

FIG. 14A is from the right ear of a pretreated, noise-exposed animal and demonstrates a narrow band of outer hair cell loss to over 90% as well as scattered inner hair cell loss. In contrast to this, FIG. 14B from left ear of a saline-noise animal demonstrates a much broader band of greater than 90% outer hair cell loss and more extensive inner hair cell loss than seen in the pre-treated ear.

DESCRIPTION OF THE PREFERRED EMBODIMENTS

Figure 1A:
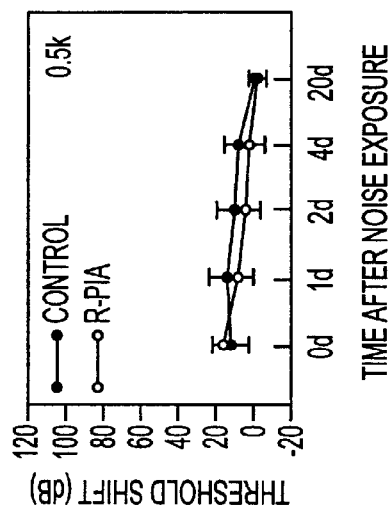
FIG. 1 is a series of graphs which depicts our experimental work with R-PIA in a chinchilla model of SNHL. A $10^{-4}$ M solution of R-PIA was placed on the round window membrane of chinchillas for thirty minutes and saline was placed as a control on round window membrane in the opposite-ear. After thirty minutes the fluids were removed, the surgical sites closed and the animals were exposed to 4 kHz octave band noise at 105 dB SPL for thirty minutes. The animals then had hearing thresholds measured at the various frequencies depicted at days 0, 1, 2, 4 and 20 using evoked potentials measured from the inferior colliculus. R-PIA treated ears showed a faster and more complete recovery of hearing thresholds than ears treated with saline. In fact there was significantly less permanent hearing threshold shift in R-PIA treated ears compared to saline treated ears at 4, 8 and 16 kHz.
Figure 1B:
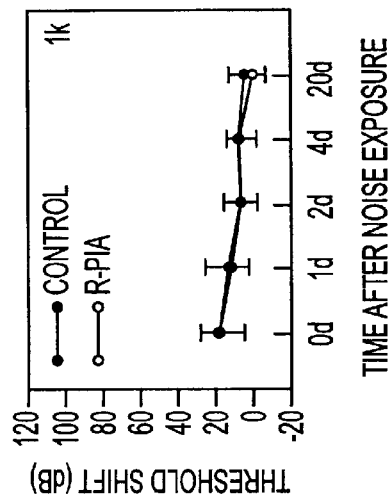
Figure 1C:
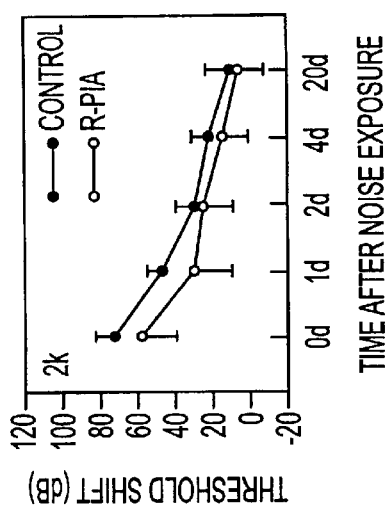
Figure 1D:
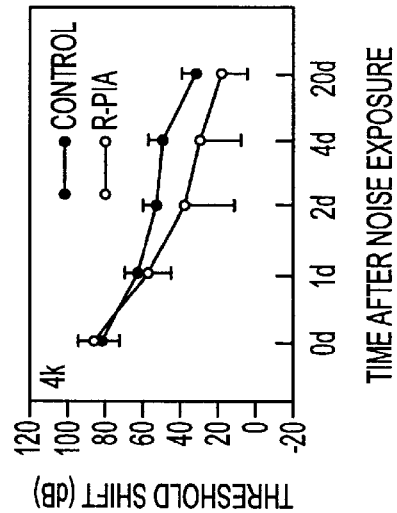
Figure 1E:
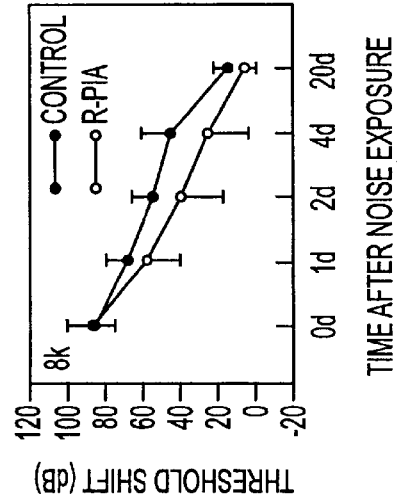
Figure 1F:
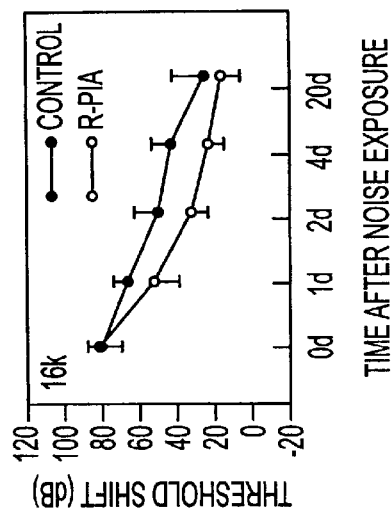

The invention is accomplished by preventing and/or reversing inner ear damage due to noise or toxins by upregulating antioxidant enzyme activity by applying agents such as R-N6-Phenylisopropyl adenosine (R-PIA) to the round window membrane of the inner ear or systemically, and/or by also applying agents such as 1–2 oxothiazolidine-4-carboxylic acid (Procysteine) to the round window membrane or by giving it systemically. Selective auditory hair cell protection in the face of gentamicin exposure by concomitant delivery of an NMDA antagonist or a trophic factor such as GDNF with the gentamicin. These and additional agents are also accomplished by curtailing activated programmed cell death pathways and/or inducing/enhancing cell repair mechanisms in the inner ear.

These agents can be administered orally, intravenously, topically onto the surface of the round window membrane of the ear, or topically elsewhere in the middle or inner ear. The preferable systemic administration method is orally and the preferable topical administration is via a catheter onto the surface of the round window membrane of the ear.

Reactive oxygen intermediates (ROI) have now been associated with deafness due to aminoglycoside antibiotics (i.e. gentamicin), chemotherapeutic agents (i.e. cisplatin), noise-induced hearing loss and closed head injury and (6, 7, 5, 8). Cisplatin and noise exposure are both associated with decreases in cochlear and hair cell reduced glutathione (GSH) a major intracellular free radical scavenger and reducing compound (9,5). Depletion of cellular GSH results in increased calcium release from intracellular stores as well as inhibition of calcium extrusion, producing a marked increase in cytosolic calcium concentration. The rise in cytosolic calcium then triggers cytotoxicity which may take the form of apoptosis (10). Oxidative stress resulting in reduced cellular GSH can lead to apoptosis in neural as well as non-neural cells (11).

Possible mechanisms by which noise may induce ROI in the cochlea may include as a secondary event to ischemia-reperfusion due to temporary vasoconstriction (12), directly from the effects of sound energy on oxygenated perilymph (13), as a result of noise-induced calcium influx through trauma-induced cell membrane microbreaks (14) or as a by-product of glutamate excitoxicity including nitric oxide (NO) and peroxynitrite ROI damage (15).

Considerable evidence is accumulating that implicates ROI in the cochlear damage associated with some acoustic trauma. Exposure of chinchillas to "conditioning" noise leads to the upregulation of the activity of several antioxidant enzymes (16). High level noise exposure is associated with accumulation of superoxide anion in the stria vascularis (17) and other ROI (18) in the cochlea. Also, noise exposure is associated with an increase in perilymph GSH levels (22), while outer hair cell GSH levels decline. As in the case of cisplatin toxicity, inhibition of GSH synthesis using buthionine sulfoximine (BSO) enhances the hair cell damage and hearing loss associated with noise exposure (18). Quirk et al. published that an antioxidant lipid peroxidase inhibitor prevented temporary threshold shifts in noise-exposed rats (19). Super oxide dismutase-polyethylene glycol and allopurinol, two free radical scavengers, were found to attenuate cochlear action potential and cochlear microphonic threshold shifts when given before and during damaging noise exposure (22). An adenosine agonist which can upregulate antioxidant enzyme activity in the cochlea can prevent outer hair cell death and permanent hearing loss in chinchilla (5) and a GSH prodrug administered prior to noise exposure was found to reduce hearing loss in guinea pigs (18). Two NMDA receptor antagonists were found to prevent auditory hair cell damage and hearing loss in animals exposed to gentamicin and other aminoglycosdes (27). The proposed mechanism is that gentamicin damages the auditory hair cells by combining with NMDA receptors for the auditory neurotransmitter glutamate causing glutamate excitotoxicity. By blocking access of the gentamicin to the NMDA receptor the NMDA antagonists prevent the glutamate excitotoxicity, hair cell loss and hearing reduction (27). Since the vestibular hair cells and neurons utilize a different neurotransmitter and receptor system the auditory hair cells can selectively be protected while gentamicin ablates the vestibular system by including an NMDA antagonist With the gentamicin or preceding the gentamicin.

Upregulating and augmenting the inner ear's defenses against ROI thus has the potential to reduce hearing loss due to all these etiologies. We have shown that enhancing inner ear antioxidant defenses can reduce inner ear cochlear hair cell loss and/or hearing loss due to noise and cisplatin and others have shown that different antioxidant strategies may reduce aminoglycoside ototoxicity.

The invention involves augmenting the inner ear's antioxidant defenses either prior to (protection) or after (rescue); the: toxic or traumatic insult by increasing inner ear antioxidant enzyme activity, by increasing the inner ear antioxidant levels, by reducing glutamate excitotoxicity or by combining these treatment modalities. More specifically, the therapeutic strategy involves increasing antioxidant enzyme levels in the inner ear through the application of agents such as the adenosine agonist R-PIA or other similar agents, or through the application of antiapoptotic agents or trophic factors (growth factors) which may also upregulate antioxidant enzyme levels. Increasing inner ear antioxidant levels would primarily be aimed at increasing inner ear glutathione (GSH) levels. By itself, GSH is relatively ineffective at increasing intracellular GSH levels as it is not well transported into most cells (23). Therefor the invention calls for utilizing compounds which can be transported into the inner ear hair cells and then synthesized into GSH. These compounds would include L-2-oxothiazolidine-4-carboxylic acid (OTC), L-N-acetylcysteine (L-NAC), methionine and S-adenosyl-L-methionine (SAMe) as well as other agents which could increase inner ear glutathione levels. GSH formation is under feed back inhibition in that adequate GSH levels inhibit the rate limiting enzyme for GSH synthesis, γ-glutamyl cysteine synthase (23). For this reason, the combination of an agent which upregulates the antioxidant enzyme activity (R-PIA upregulates γ-glutamyl cysteine synthase activity in the inner ear) with a substrate for GSH (i.e. OTC) is more likely to have a protective or rescue effect on the inner ear when ROI are involved in creating damage. This invention would include the use of a combination of agents such as the addition of uric acid as a free radical scavenger or single agents depending on safety and efficacy. These agents might be delivered systemically, in the middle ear or directly in the inner ear. NMDA antagonists would include agents such as dizocilpine or ifenprodil or similar agents (27).

Upregulating adenosine effects in the inner ear may have additional beneficial effects other than upregulating antioxidant enzyme activity. Adenosine upregulation in neural tissue has been demonstrated to decrease release of potentially damaging excitotoxic amino acids (24) such as glutamate (the primary cochlear neurotransmitter) and thereby limit NO production and damage (25). Also seen is a beneficial vasodilator effect, calcium homeostasis maintenance effect and a cell membrane stabilizing effect (24). Given systemically, adenosine agonists may have unwanted side effects including hypotension, cardiac depression and hypothermia and these agents may not cross from the blood to the inner ear through the blood labyrinthine barrier (26). These problems may be dealt with by applying the drug to the round window membrane, by utilizing drugs such as acadesine and AICA Riboside which act as an adenosine agonist only in ischemic tissues (30,31) or by utilizing adenosine agonists that have specific uptake in the inner ear. Adenosine effects can also be increased by blocking adenosine breakdown using adenosine deaminase inhibitors (24).

Many of the GSH substrates and adenosine agonists have a short effective or systemic half-life. Therefor this invention may include the use of embodiments that increase the effective half-life of the drug when given systemically and may include an infusion device or pump or sustained release polymer for sustained systemic release.

Having described the invention, the following examples are given to illustrate specific applications of the invention including the best mode now known to perform the invention. These specific examples are not intended to limit the scope of the invention described in this application.

This invention functions to prevent or reverse toxic or noise induced hearing loss (SNHL) through biologic mechanisms. Reactive oxygen intermediates (ROI) are responsible for inner ear damage due to loud noise and toxins. Inner ear damage due to ROI can be reduced by augmenting the inner ear's antioxidant defenses. The invention involves preventing and/or reversing inner ear damage due to toxins or noise by upregulating antioxidant enzyme activity by applying adenosine agonists such as R-N6-Phenylisopropyl adenosine (R-PIA), acadesine or adenosine deaminase inhibitors to the round window membrane of the inner ear, and/or by also applying 1-2-oxothiazolidine-4-carboxylic acid (Procysteine) or other glutathione prodrugs to the round window membrane or by giving them systemically with or without free radical scavengers such as uric acid (32). The agent(s) may be applied before, during or after the noise trauma or toxic exposure. Selective protection of auditory hair cells in patients receiving intratympanic gentamicin therapy by preceding the gentamicin therapy with an NMDA antagonist and giving it concomitantly with the gentamicin in the same vehicle. Currently there is no published effective medication to prevent or reverse SNHL. This invention differs from mechanical noise attenuators or hearing protection devices in that it does not need to be worn and does not decrease hearing acuity as hearing protectors do. Also, this treatment has the potential to reverse SNHL after it is occurred.

Many specific clinical examples for the use of these therapies can be described. Workers in a high-risk noise environment could be given oral agents to enhance antioxidant ear defenses prophylactically. Persons exposed to unexpected loud noise with subsequent hearing loss could be given systemic or intraear therapies to rescue and reverse the hearing loss. Patients receiving cisplatin or aminoglycoside antibiotics or other drugs with potential ear toxicities could be given the protective agents before, during or after the toxin to prevent or reverse hearing loss. Patients with Meniere's disease undergoing intratympanic gentamicin therapy could be given NMDA antagonists with or without other protective agents at the same time or preceding the gentamicin therapy, possibly in the same delivery vehicle.

Having described the invention the following examples are given to illustrate specific applications of the invention including the best mode now known to perform the invention.

EXAMPLE 1

Figure 2A:
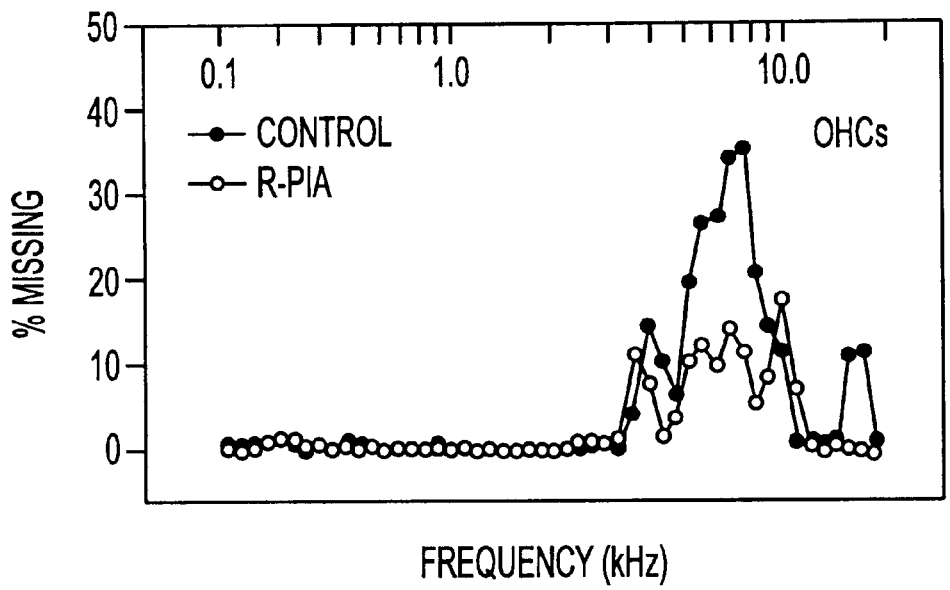
FIG. 2 is two graphs which depicts the data from these same animals showing inner and outer hair cell losses. Inner hair cell losses were minimal in both conditions but there was a fourfold reduction in outer hair cell loss in the R-PIA treated ears compared to saline control ears consistent with the reduction in hearing loss seen in ears treated with R-PIA. The details of this study have been submitted and recently accepted for publication in a peer-reviewed journal (5).
Figure 2B:
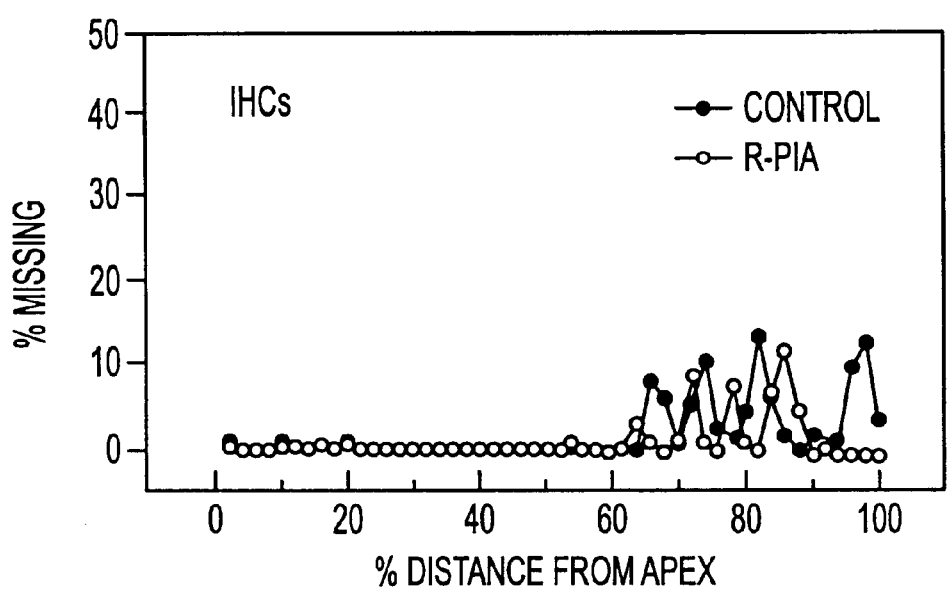

In figure one noise induced permanent threshold shifts were prevented in the Chinchilla model by the application of a dilute ($10^{-4}$ molar) solution of R-PIA directly onto the round window membrane for thirty minutes. What is demonstrated in this figure is a significant reduction in permanent hearing loss in the R-PIA treated ears compared to control ears. FIG. 2 shows that the R-PIA treated ears had a four-fold reduction in outer hair cell loss compared to control ears. These data of hair cell counts are from the same animals which underwent hearing testing.

EXAMPLE 2

Figure 3:
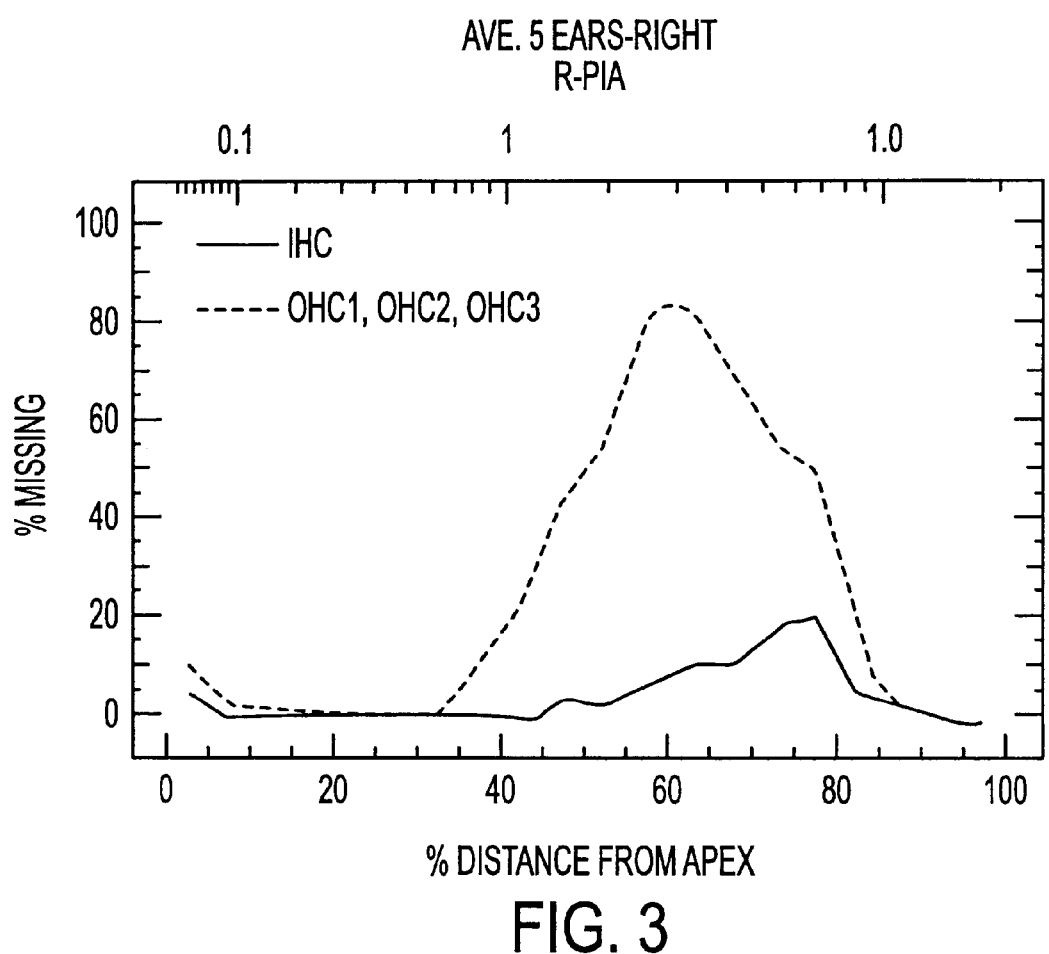
FIG. 3 is a graph depicting the percentage of missing hair cells from animals receiving round window membrane RPIA treatment in the right ear, as above, after impulse noise exposure mimicking a 50-salvo volley of M-16 fire.
Figure 4:
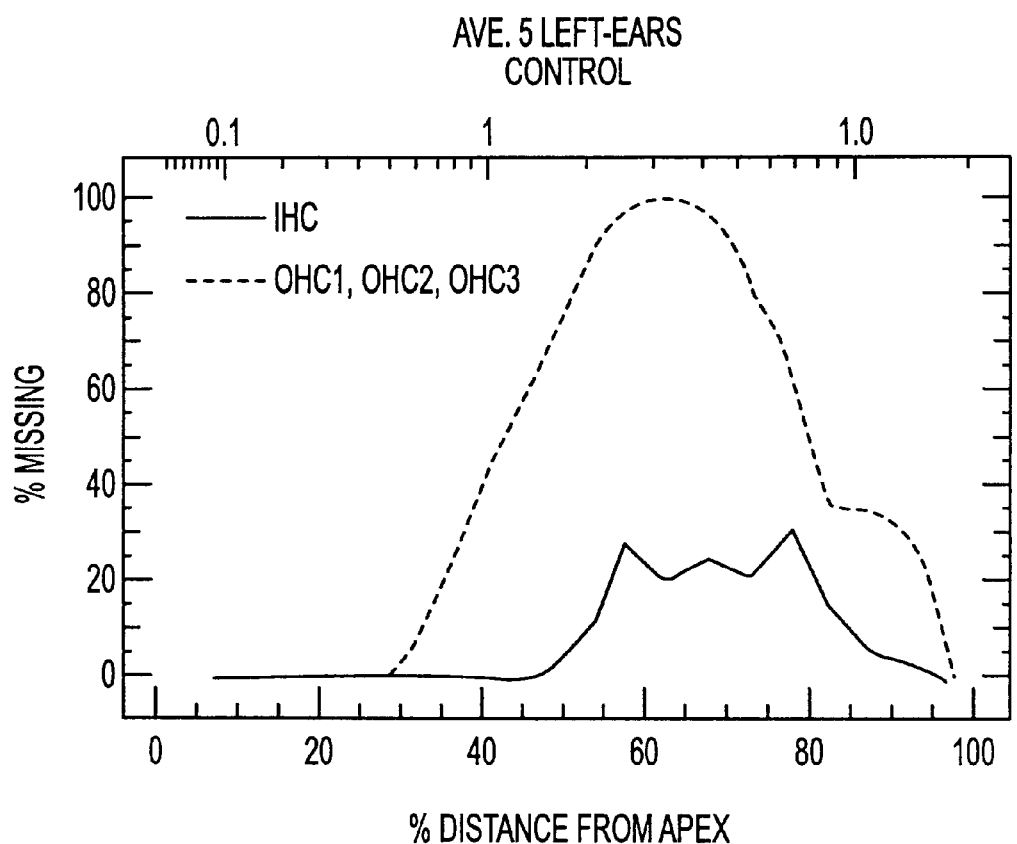
FIG. 4 is a graph depicting the percentage of missing hair cells from the left (untreated ear) of the same animals, as above, after impulse noise exposure mimicking a 50-salvo volley of M-16 fire.

FIGS. 3 & 4 illustrate data from Chinchilla exposed to simulated M-16 rifle fire impulse noise (50-salvo volleys). These animals received R-PIA treatment as outlined above (by the application of a dilute ($10^{-4}$ molar) solution of R-PIA directly onto the round window membrane for thirty minutes) with saline as a control on the round window membrane of the opposite ear. FIGS. 3 and 4 depict the percentage of missing inner and outer hair cells quantified in the inner ears of animals euthanized after the noise exposure. These figures demonstrate a significant reduction of inner and outer hair cell loss in the R-PIA treated ears compared to control ears.

Experimental results show a reduction of permanent hearing loss in R-PIA treated ears as compared to saline treated (control) ears at a variety of different frequencies. Other tests show a reduction of permanent hearing loss in R-PIA treated ears as compared to ears that received no treatment. The results of both these tests show the frequency specific evoked potential threshold shifts from the same Chinchilla prior to and after noise exposure (out to 20 days post-exposure). These results demonstrate a significant reduction in permanent hearing loss at a number of different frequencies.

EXAMPLE 3

Figure 5:
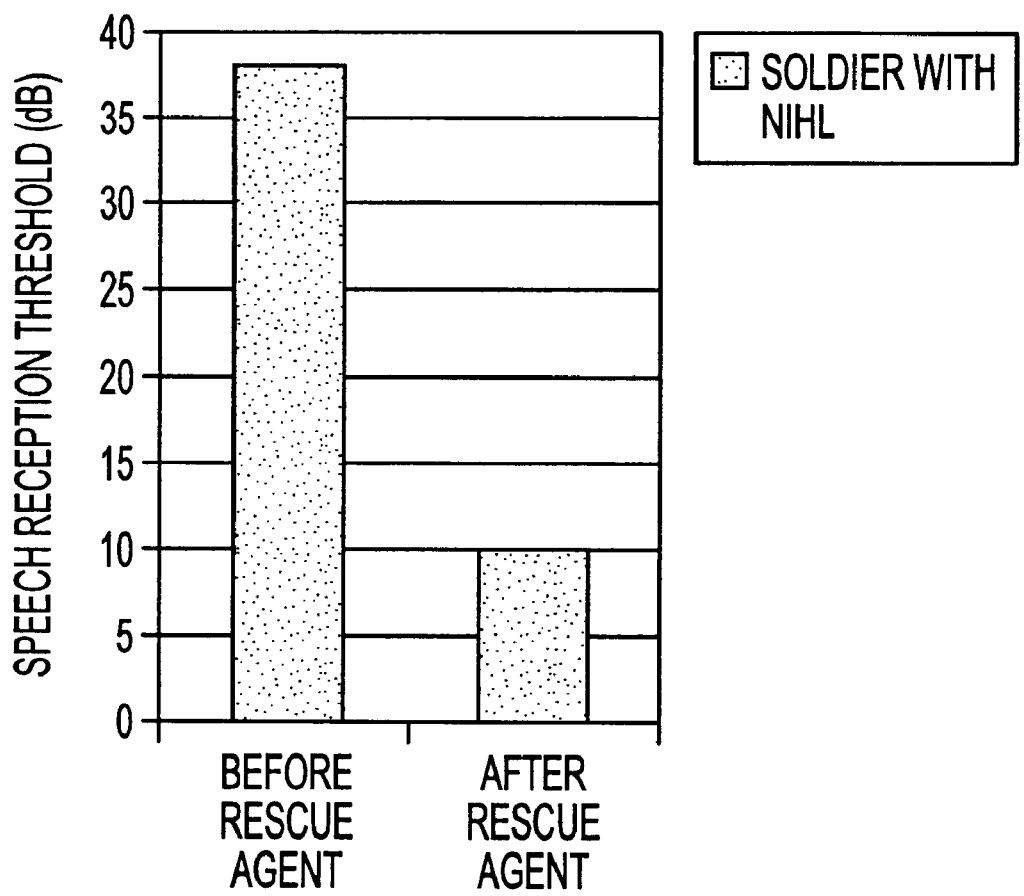
FIG. 5 is a bar graph comparing the speech reception threshold values of an individual who suffered noise induced hearing loss before and after administration of an oral rescue agent.
Figure 6:
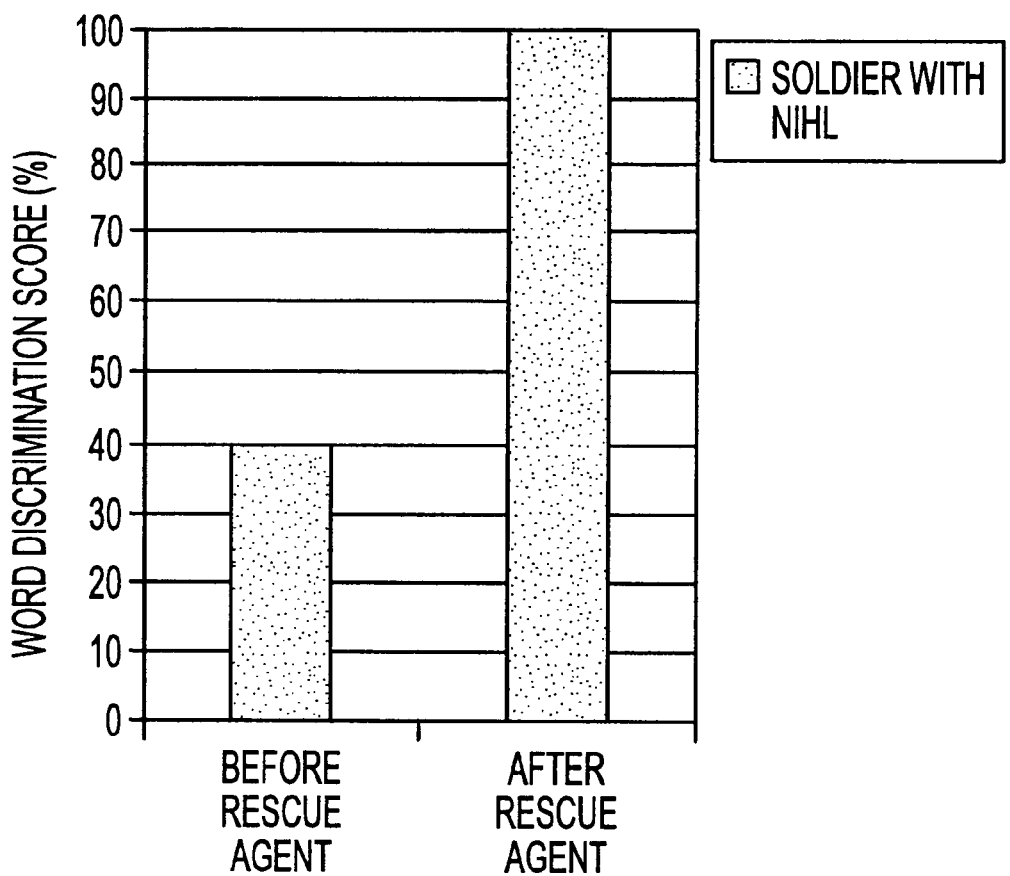
FIG. 6 is a bar graph comparing the word discrimination scores of an individual who suffered noise induced hearing loss before and after administration of an oral rescue agent.
Figure 7:
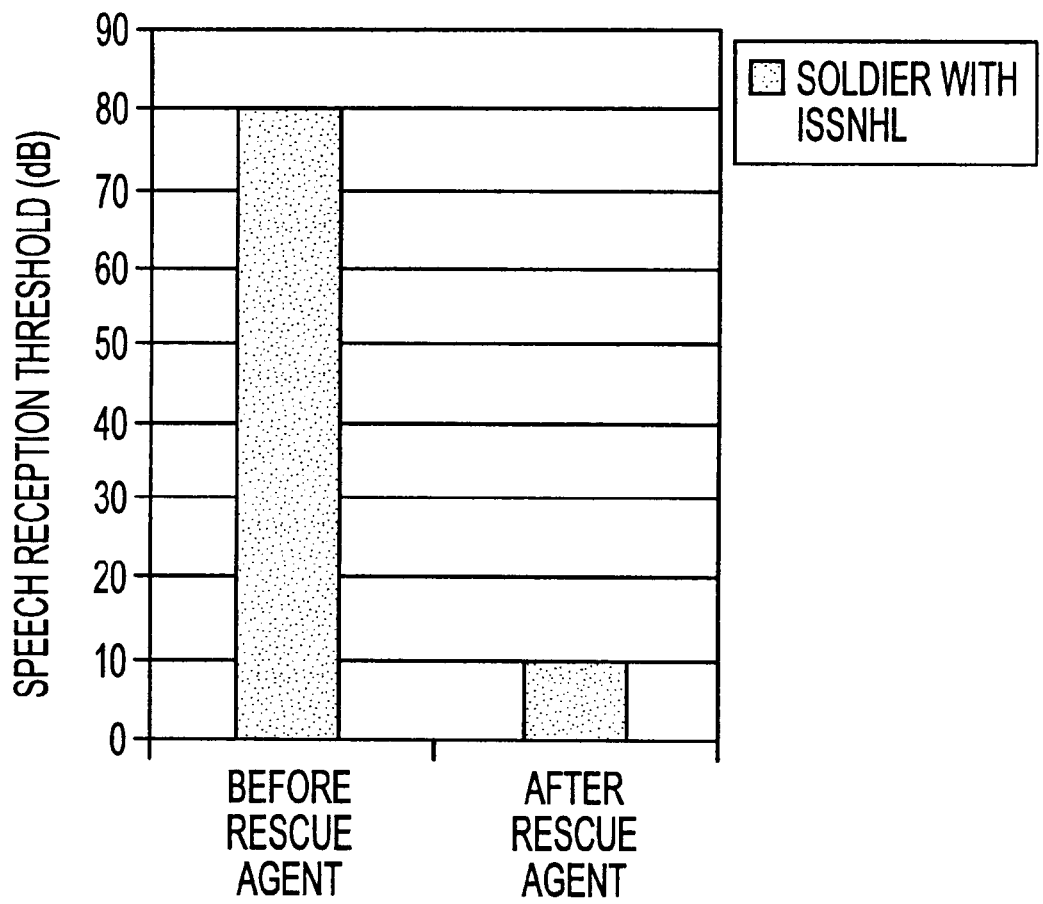
FIG. 7 is a bar graph comparing the speech reception threshold values of an individual who suffered an idiopathic sensorineural hearing loss before and after administration of a topical rescue agent.

An Army Infantryman lost his hearing protection in one ear during a live fire training evolution. He suffered a moderate to severe hearing lost in the effected ear. He received treatment in the form of ant initial dose of 70 mg/kg of L-N-acetyl cysteine (LNAC) by mouth followed by 35 mg/kg LNAC by mouth QID for seven days. FIG. 5 depicts the complete recovery of a moderately elevated speech reception threshold. FIG. 6 depicts the complete recovery of a severely impaired word discrimination ability. Our conclusion is that this soldier's hearing recovered after administration of this agent. This degree of hearing recovery is greater than usually seen with this degree of hearing impairment due to noise.

EXAMPLE 4

Figure 8:
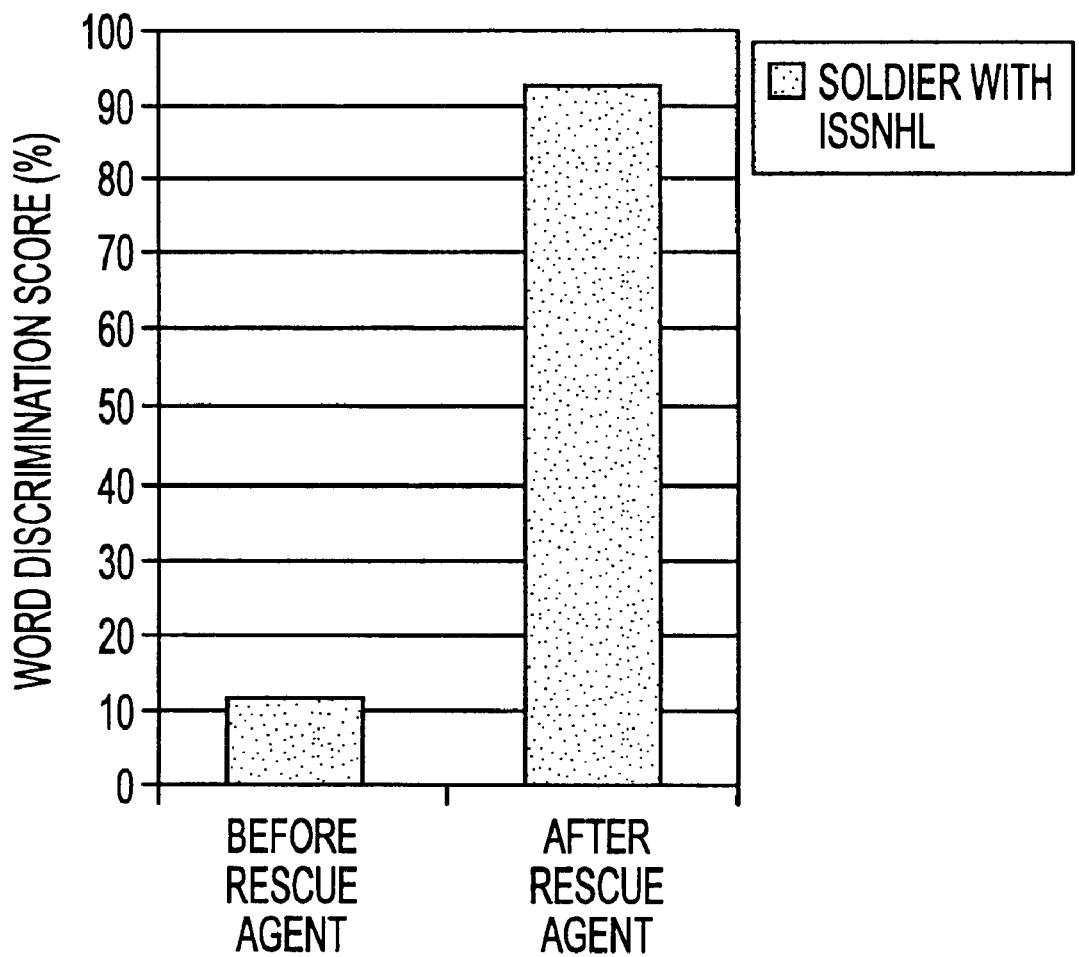
FIG. 8 is a bar graph comparing the word discrimination scores of an individual who suffered an idiopathic sensorineural hearing loss before and after administration of a topical rescue agent.
Figure 9:
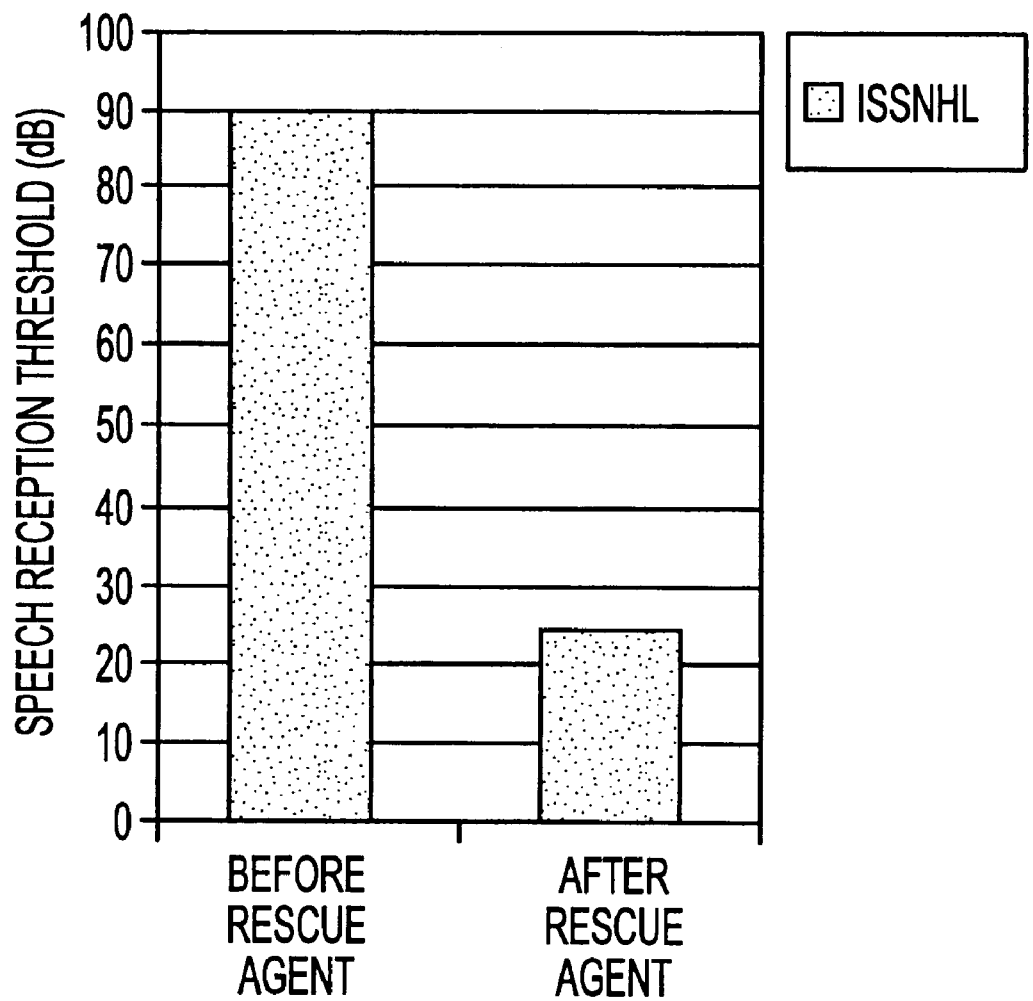
FIG. 9 is a bar graph comparing the speech reception threshold values of another individual who suffered an idiopathic sensorineural hearing loss before and after administration of a topical rescue agent.

A 43 year old Army Sergeant noted the sudden onset of a severe hearing loss and tinnitus in her left ear. She was initially given one week of conventional therapy with oral prednisone and a trial of close observation. She had no response to this treatment regimen and two weeks after experiencing the hearing loss she was treated with topical methylprednisolone. The topical methylprednisolone was administered in a round window microcatheter (IntraEar Corporation, Denver, Colo.) via a method developed by our group. The methylprednisolone was given in a concentration of 125 mg/ml. The catheter was pre-loaded with 0.125 ml of this compound after the catheter was secure in the round window niche. The catheter was then attached to a battery operated pump (Disetronics, Inc) which pumped the methylprednisolone into the catheter at 10 ul/hour for 14 days. FIG. 9 depicts the complete recovery of the severely elevated speech reception threshold back to normal levels. FIG. 8 depicts the complete recovery of the profoundly impaired word discrimination ability after administration of the medicine. The patient's tinnitus was completely resolved after treatment. Since this individual had failed conventional therapy, the outlook for recovery without the new treatment was less than 15%.

EXAMPLE 5

Figure 10:
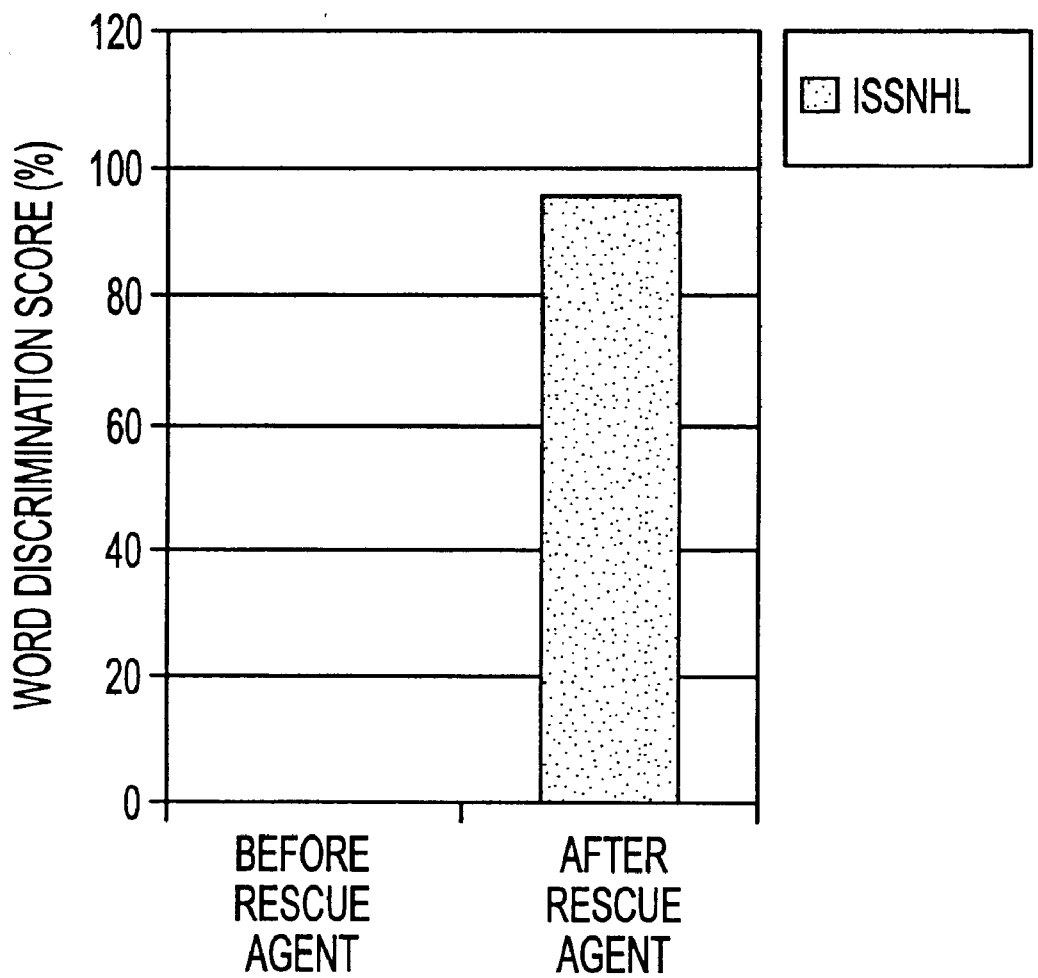
FIG. 10 is a bar graph comparing the word discrimination scores of another individual who suffered an idiopathic sensorineural hearing loss before and after administration of a topical rescue agent.

A 48 year old Ophthalmologist noted the sudden onset of a severe hearing loss and tinnitus in his right ear. He was initially given three weeks of conventional therapy with oral prednisone for 10 days and a trial of close observation. He had no response to this treatment regimen and three weeks after experiencing the hearing loss he was treated with topical methylprednisolone. The topical methylprednisolone was administered in a round window micro-catheter (IntraEar Corporation, Denver, Colo.) via a method developed by our group. The methylprednisolone was given in a concentration of 125 mg/ml. The catheter was pre-loaded with 0.125 ml of this compound after the catheter was secure in the round window niche. The catheter was then attached to a battery operated pump (Disetronics, Inc) which pumped the methylprednisolone into the catheter at 10 ul/hour for 14 days. FIG. 9 depicts the complete recovery of the profoundly elevated speech reception threshold back to normal levels. FIG. 10 depicts the complete recovery of the profoundly impaired word discrimination ability after administration of the medicine. The patient's tinnitus was completely resolved after treatment. Since this individual had failed conventional therapy, the outlook for recovery without the new treatment was less than 15%.

EXAMPLE 6

Figure 11:
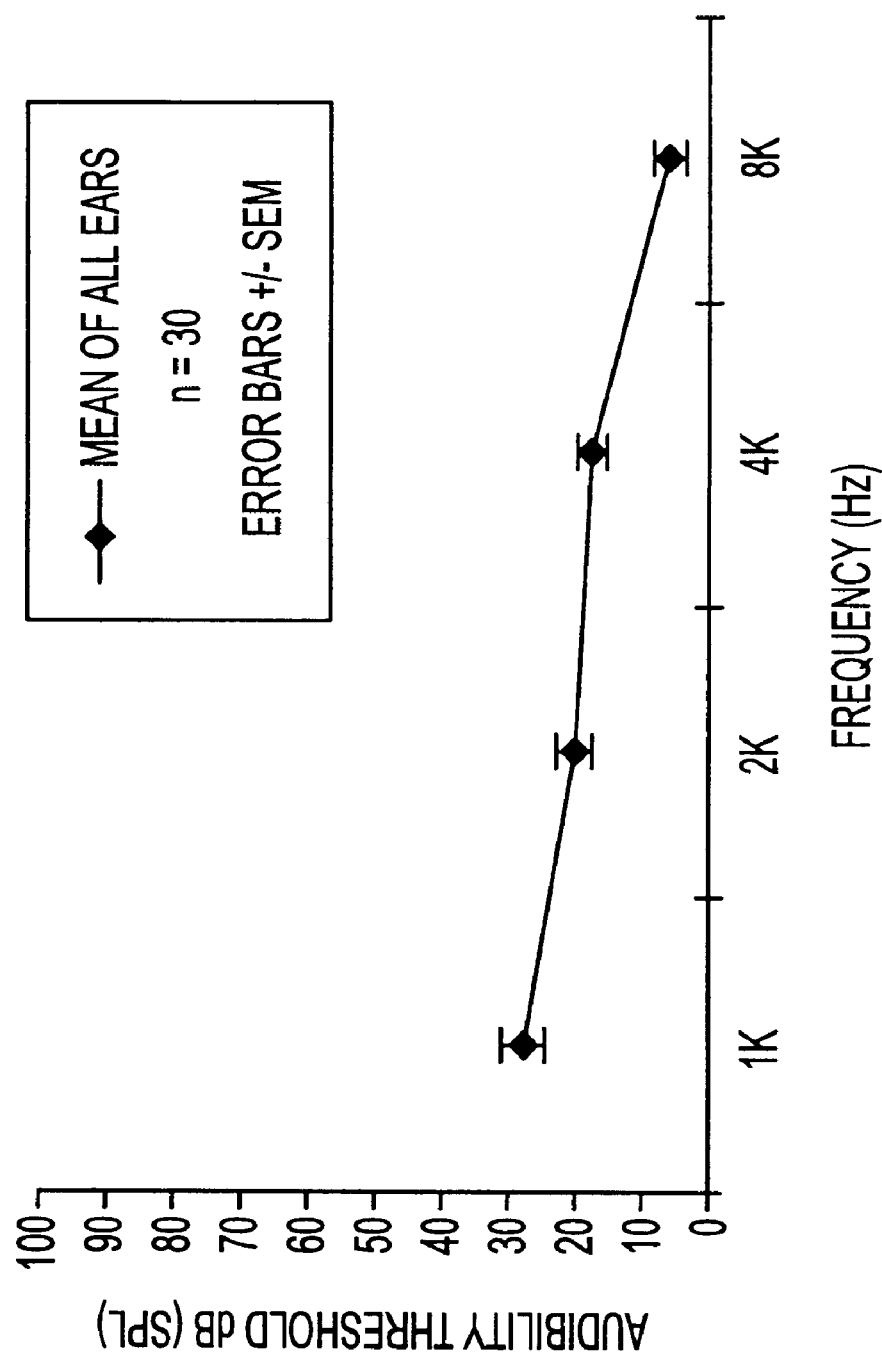
FIG. 11 shows the pre-noise audibility thresholds derived from inferior colliculus evoked potentials for the subjects of this study are shown for 1, 2, 4, and 8 kHz frequencies. The audibility thresholds range from a high of 28-dB sound pressure level (SPL) at 1 kHz to a low of 5.3 dB SPL at 8 kHz. These are mean values of sums of left and right ears prior to noise exposure. There were a total of 15 subjects and 30 ears. Error bars represent standard error of the means.

Fifteen female adult chinchilla laniger were divided equally into three experimental groups. Each animal received inferior colliculus electrode implants one week prior to noise exposure. Baseline hearing thresholds were taken within two days of the initial noise exposure (FIG. 11). The three groups consisted of a saline control group, a pre-noise treatment group, and a post-noise treatment group, the latter two hereafter referred to as "pre-treatment" and "post-treatment" groups.

Pre-treatment animals received N-L-acetylcysteine (325 mg/kg) and salicylate (50 mg/kg) by intraperitoneal injection one-hour prior and one hour following noise exposure and then twice per day (bid) the following two days. The post-treatment group received the same dosage, although in this case at one hour following noise and bid the ensuing two days. Saline-noise animals were injected with a similar volume of saline over the same schedule as the post-treatment group. All three groups had audiologic tests performed pre-noise, one-hour post noise, and once a week for three weeks. Shortly after the last audiometric determination, animals were humanely euthanized, and the temporal bones were harvested and subsequently stained with a vital dye to indicate the presence of living hair cells. The care and the use of the animals in this study were approved by the Animal Care and Use Committee of Naval Medical Center San Diego in accordance with the guidelines of the Declaration of Helsinki.

2.1. Inferior Coiicidus Electrode Placement

Animals were anesthetized with a ketamine/xylazine mixture and placed in a stereotactic head holder. Fur covering the cranium was removed and a midline scalp incision was made. Periosteum was stripped from the calvarium, and the underlying bone was treated with silver nitrate solution (10%) and then coated with cyanoacrylate cement. Using a diamond burr and high-speed drill, a 1 mm burr-hole was produced 1 mm anterior, and lateral to bregma. A 0.5-cm Teflon-coated tungsten rod electrode (reference) was then inserted and fixed using dental cement. Two more burr holes were drilled 1-mm lateral to midline and 5 mm anterior to the bullac. Using a micromanipulator, two 1-cm Teflon-coated tungsten rod electrodes were inserted individually. Electrode placement was confirmed using a real-time click-evoked auditory brainstem voltage response. The electrode was then fixed in place with dental cement. The skin wound was allowed to granulate around the skullcap. All animals received an antibiotic prophylactically for 72 hours post-operatively (enrofloxacin, 2.5 mg/kg by intra-museular injection).

2.2. Evoked Potential Measurement

Animals were awake and lightly restrained in a plastic tube during the 30 minute recording procedure. Digitally generated stimuli consisted of tone pips (4 ms Blackman rise/fall ramp, 0 ms plateau, and constant alternating phase) at octave intervals 1, 2, 4, and 8 kHz. All acoustic stimuli were routed through a computer-controlled attenuator to an insert earphone (Etymotic Research ER-2). The sound delivery tube of the insert earphone was positioned approximately 5 mm from the tympanic membrane. Earphone sound delivery was calibrated using a coupler attached to the sound level meter approximating the distance from the earphone to the tympanic membrane. Five hundred samples were collected from the recording electrode, amplified (50,000–75,000×), filtered (100–1500 Hz), and fed to an A/D converter computerized on a signal processing board. Stimuli at a rate of 23/sec were varied in 10-dB descending steps, until threshold was reached, then 5-dB ascending steps were presented to confirm threshold. Earphone inserts on the tested ear were removed, and controls during which no sound was presented were determined for comparisons. Threshold was defined as the mid-point between the lowest level at which a clear response was evidenced and the next lower level where no response was observed.

2.3. Noise Exposure

One week was allowed to elapse after placement of the IC electrode in order to allow surgical healing prior to noise exposure. Our protocol was developed from the procedure of Hu et al. *Hear Res*, 113, 198–206 (1997). Specifically, an octave band noise centered at 4 kHz was generated by a standard audiometer (GSI 16), selected to white noise, routed through an attenuator (HP 350 D), a band-pass filter (Krohn-Hite 3550R), and a power amplifier (Crown D150A model 716) to an audiometric loudspeaker suspended directly above the animal's cage. The sound spectrum output of the system was confirmed using a Larson and Davis model 800B sound level meter, centering the octave bandwidth at 4 kHz. In order to ensure consistent noise exposure conditions, the noise output of the system was periodically monitored using a sound level meter (Larson and Davis 800B). Also, a pre-amplifier (Larson and Davis model 825), and a condenser microphone (Larson and Davis, LDL 2559), were positioned within the cage at the level of the animal's head. Each animal was exposed continuously to the noise at a level of 105 dB SPL for six hours. During the noise exposure, the animal was unrestrained in a small wire cage with ad-lib food and water access. When the animals were not being exposed to noise, they were housed in a quiet animal colony.

2.4. Histologic Examination

Following auditory tests (i.e. at three weeks post noise exposure), the animals were heavily anesthetized with ketamine (30 mg/kg) and Xylazine (1 mg/kg). Each temporal bone was quickly removed from the skull. The cochlea was exposed and slowly perfused through the oval window and round window with a solution of 0.2 M sodium succinate and 0.1% nitrotetrazolium blue in 0.2 M phosphate buffer (pH=7.4 at 37° C.). Samples were then immersed in the same solution for one hour at 37° C. Lastly, the cochlea was rinsed with buffer and fixed with 4% paraformaldehyde for 24 hours. Cochleae were dissected and sections of the organ of Corti were mounted on glass slides and examined for hair cell loss under a light microscope at 400× magnification. Missing or non-viable hair cells were noted by the absence of blue vital stain in the area of inner and outer hair cells. An experienced but experiment-blinded observer counted missing hair cells over the length of the basilar membrane per cochlear turn utilizing specialized software. A cytocochleogram was developed for inner and outer hair cells for each cochlea and cytocochleogram means were computed and graphed.

2.5. Statistical Analyses

A 3-way ANOVA with interaction model was used for analyzing the effect on hearing thresholds over time for each ear being treated as repeated measures. Where a significant effect included more than two levels, pair-wise comparisons of the levels were made by Scheff methods (post hoc test). A one way ANOVA was used to analyze the hearing threshold data at the three-week time point at the termination of the experiment, and the Newman Keuls multiple comparison tests (post hoc) were used to analyze the hearing threshold treatment effects when significant differences were identified. To analyze cytocochleogram statistics, the area under the curve representing missing inner or outer hair cells was determined for each cochlea using AutoSketch R2 for Windows (Autodesk, Inc.). Mean areas under the curve were compared across treatment groups using one-way ANOVA. When differences were found, Tukey's post hoc analysis was applied to identify significant differences. A p-value smaller than 0.05 was considered significant.

3. Results 3.1. Audiometry

Baseline audibility threshold averages for both right and left ear evoked potentials at 1, 2, 4 and 8 kHz are represented in FIG. 11. Thresholds ranged from a maximum of 28 to a minimum of 8 dB SPL at 1 to 8 kHz, respectively. These thresholds are consistent with independently published normative data (Henderson et al., *J Acoust Soc Am*, 54, 1099–1101(1973); Hu et al., *Hear Res*, 113, 198–206 (1997)).

Auditory threshold shifts (group means for left and right ears) were displayed (FIGS. 12A–D) as post-noise thresholds (dB SPL) minus baseline threshold (dB SPL). Means were plotted as a function of treatment group (saline-noise, antioxidant pre-treatment and antioxidant post-treatment), over time (zero, one, two, three wk.) and by threshold test frequency (1,2,4, and 8 kHz).

Figure 12A:
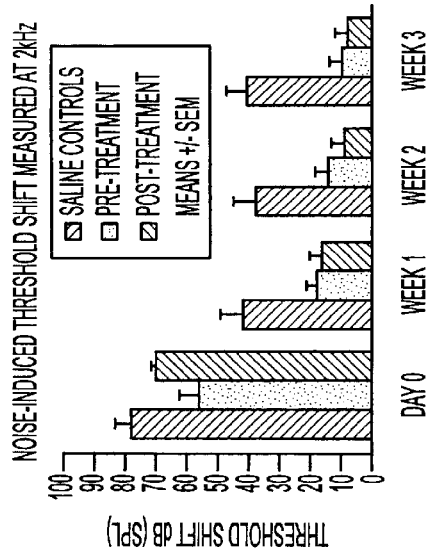
FIGS. 12A–D show audibility threshold shifts measured at 1, 2, 4, and 8 kHz after a 6 hour 4 kHz octave band noise exposure at 105 dB SPL, as a function of time, test frequency, and treatment group. Threshold shift was calculated as the threshold for a particular frequency at a time point after noise exposure minus the baseline threshold for that frequency in dB SPL. Thresholds at time point day zero were obtained one hour after exposure. The data depicts means of left and right ears of five animals (10 ears) in each group for a total of N=15 (30 ears). Initial threshold shifts at day zero were equivalent for saline-noise and post-treatment groups at all frequencies except at 1 kHz where the initial threshold shift was reduced for the post-treatment group. The initial threshold shifts were reduced for the pre-treatment group compared to the saline-noise group at all frequencies. There was recovery of threshold shift among all three groups. However, the threshold shift recovery for the saline-noise group tended to plateau over weeks two and three. In contrast, the permanent threshold shifts that were observed for the pre and post-treatment groups were reduced significantly ($p<0.05$) compared to the saline-noise group. The threshold shift at three weeks for saline-noise animals varied between 20 and 40 dB SPL from 1 to 8 kHz. The permanent threshold shift for the pre-treatment animals was significantly reduced to about 0–10 dB. The permanent threshold shift for the post-treatment group at three weeks was similar to the pre-treatment group at 1 and 2 kHz (0 to 10 dB)] (FIGS. 12A and 12B) but was intermediate between the saline-noise and pre-treatment groups at 4 and 8 kHz (23 dB) (FIGS. 12C and 12D). The post-treatment effect at 1 kHz may be explained by the reduced initial threshold shift seen at 1 kHz. Error bars represent standard error of the means.
Figure 12B:
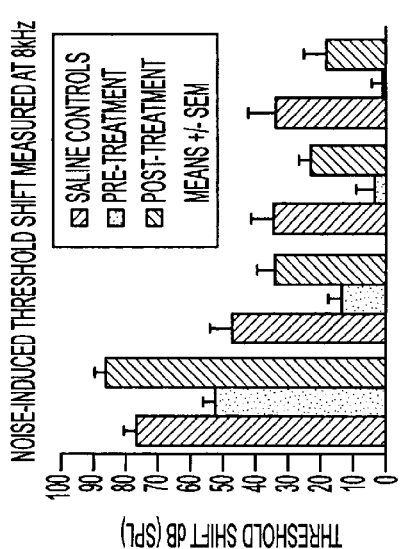
Figure 12C:
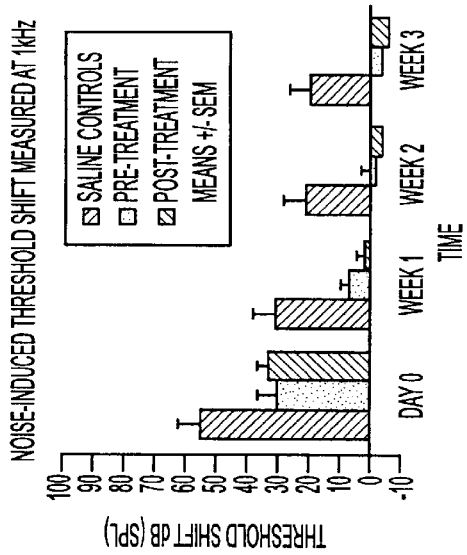
Figure 12D:
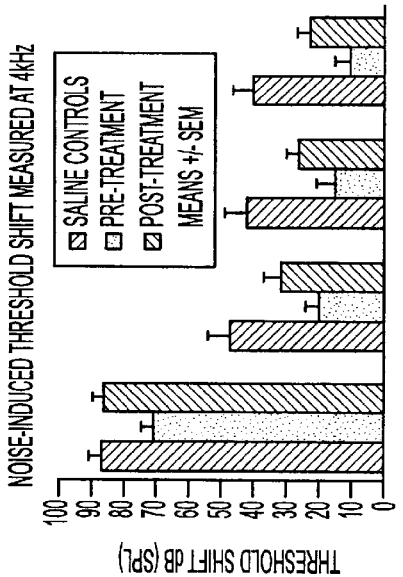

As shown (FIGS. 12A–D), six-hour sound exposure produced an initial threshold shift ranging from approximately 55 dB at 1 kHz (FIG. 12A) to approximately 80 dB at the higher frequencies (FIGS. 12B–D). The post-treatment group receiving the antioxidants one hr after exposure demonstrated threshold shifts similar to those of the saline-noise group except at 1 kHz, where the shift was only 33 dB. This suggests that the antioxidants were able to reduce temporary threshold shifts induced in this model given that noise exposure was standardized and calibrated for all groups. There was evidence of recovery of threshold shift among all three groups. However, the threshold shift recovery for the saline-noise group stabilized over weeks two and three, resulting in no significant threshold improvement for any of the frequencies tested. In contrast, both the pre- and post-treatment groups showed statistically significant improvement over the entire time period for all frequencies except 1 kHz (see Table 1), where the interaction effect with time was not significant (p=0.739). There was an overall treatment effect for both pre- and post-treatment at 1 kHz compared with the saline-noise condition ($F_{2,28}$=7.4678; p=0.013 and p<0.01, respectively on post hoc analysis—see Table 1), but the former two conditions effects were not statistically different from each other. Hearing thresholds at 1 kHz improved compared to saline-noise from week zero to week one, and from week one to week two, but not from week two to week three. This finding diminished the comparison of the treatment conditions with time.

TABLE 1

Summary of Threshold Shift Statistical Results

| | F | p ** | df |
|---|---|---|---|
| 1 kHz | | | |
| Treatment (overall effect) | 7.4678 | <0.01 | 2, 28 |
| Pre-treatment * | | .013 | 2, 28 |
| Pre-treatment by time | .5869 | ns | 6, 24 |
| Pre-treatment at 3 weeks * | 10.680 | <0.001 | 2, 28 |

TABLE 1-continued

Summary of Threshold Shift Statistical Results

|  | F | p ** | df |
|---|---|---|---|
| Post-treatment * |  | .008 | 2, 28 |
| Post-treatment by time | .5869 | ns | 6, 24 |
| Post-treatment at 3 weeks * | 10.680 | <0.001 | 2, 28 |
| 2 kHz |  |  |  |
| Treatment (overall effect) | 7.6273 | <0.01 | 2, 28 |
| Pre-treatment * |  | 0.007 | 2, 28 |
| Pre-treatment by time | 5.0637 | <0.001 | 6, 24 |
| Pre-treatment at 3 weeks * | 9.285 | <0.01 | 2, 28 |
| Post-treatment * |  | 0.013 | 2, 28 |
| Post-treatment by time | 5.0637 | <0.001 | 6, 24 |
| Post-treatment at 3 weeks * | 9.285 | <0.01 | 2, 28 |
| 4 kHz |  |  |  |
| Treatment (overall effect) | 6.6610 | <0.01 | 2, 28 |
| Pre-treatment * |  | 0.005 | 2, 28 |
| Pre-treatment by time | 3.8650 | <0.001 | 6, 24 |
| Pre-treatment at 3 weeks * | 8.151 | <0.01 | 2, 28 |
| Post-treatment * |  | ns | 2, 28 |
| Post-treatment by time | 3.8650 | <0.001 | 6, 24 |
| Post-treatment at 3 weeks * | 8.151 | <0.05 | 2, 28 |
| 8 kHz |  |  |  |
| Treatment (overall effect) | 9.1020 | <0.01 | 2, 28 |
| Pre-treatment * |  | 0.002 | 2, 28 |
| Pre-treatment by time | 2.9589 | <0.001 | 6, 24 |
| Pre-treatment at 3 weeks * | 6.8050 | <0.001 | 2, 28 |
| Post-treatment * |  | ns | 2, 28 |
| Post-treatment by time | 2.9589 | <0.05 | 6, 24 |
| Post-treatment at 3 weeks * | 6.8050 | ns | 2, 28 |

\* compared to saline control
\*\* post hoc analysis
ns = not significant

As seen in FIGS. 12A–D, the permanent threshold shift observed for the pre and post-treatment group was reduced compared to that of the saline-noise group. The threshold shift at three weeks for controls varied between 20 and 40 dB SPL from 1 to 8 kHz. The permanent threshold shift for the pre-treatment animals was significantly reduced to approximately 0–10 dB. The permanent threshold shift for the post-treatment group at three wk. was similar to the pre-treatment group at 1 and 2 kHz (0 to 10 dB) but was intermediate between the saline-noise and pre-treatment groups at 4 and 8 kHz (23 dB). Threshold shift for the pre-treatment group was significantly lower at 1, 2, 4 and 8 kHz, (p<0.05) for treatment effects averaged over time as evidenced by application of two-factor repeated measure ANOVA. The post-treatment group effect reached significance at 1, 2, 4, and 8 kHz, when week three was compared to week one (p<0.05). The effect at 1 kHz may be explained by the reduced initial threshold shift observed in the post-treatment group at 1 kHz.

3.2. Hair Cell Counts

Figure 13B:
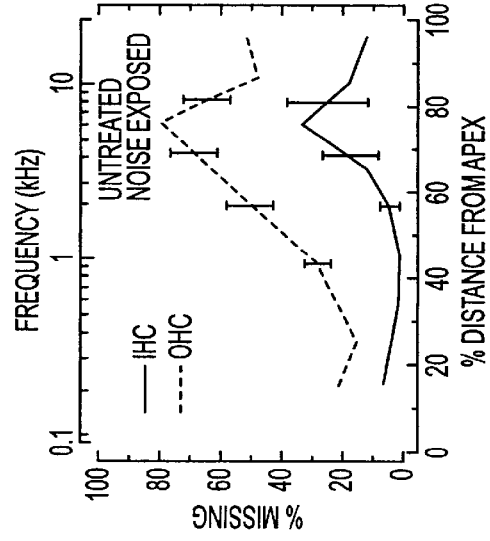
FIGS. 13A–D graphically depict mean inner and outer hair cell losses in a cytocochleogram which graphs mean percent missing hair cells on the Y axis as a function of percent distance from the cochlear apex and associated frequency region of the cochlea on the X axis.
Figure 13A:
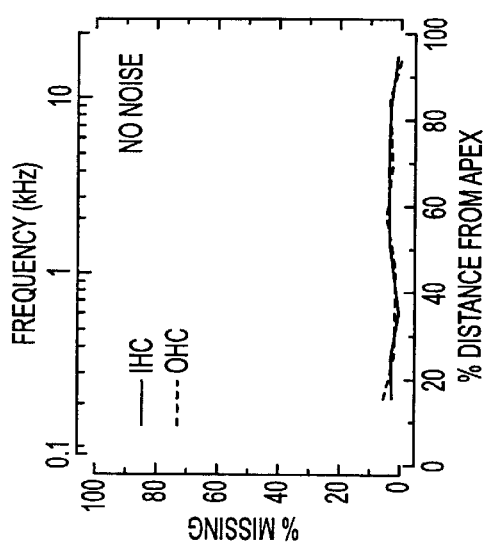
Figure 13D:
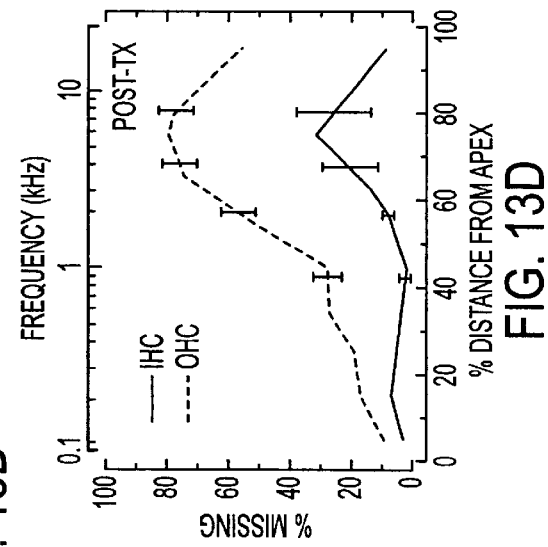
Figure 13C:
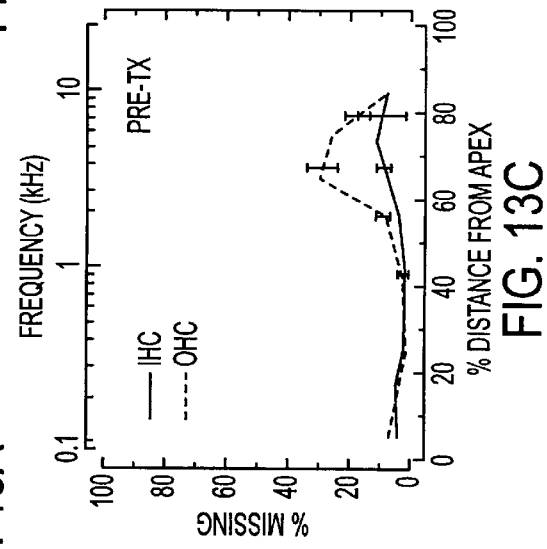
Figure 14A:
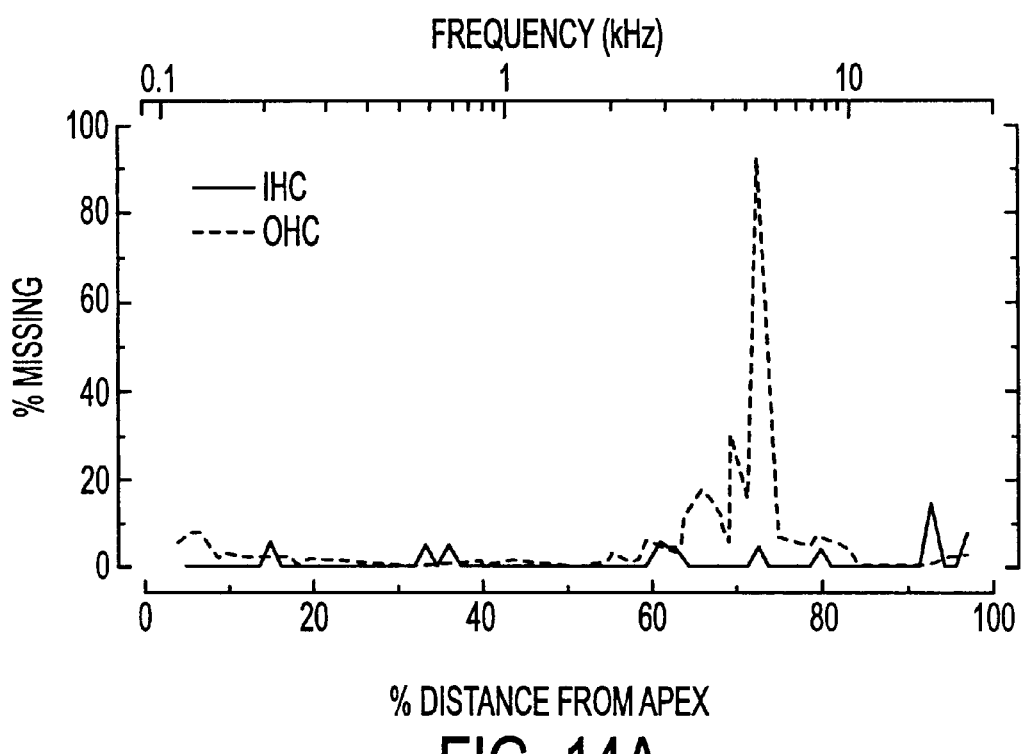
FIGS. 14A–B are cytocochleograms depicting percent missing inner (solid line) and outer (dashed line) hair cells as a function of % distance along the basilar membrane from the apex, also correlated with frequency response range.
Figure 14B:
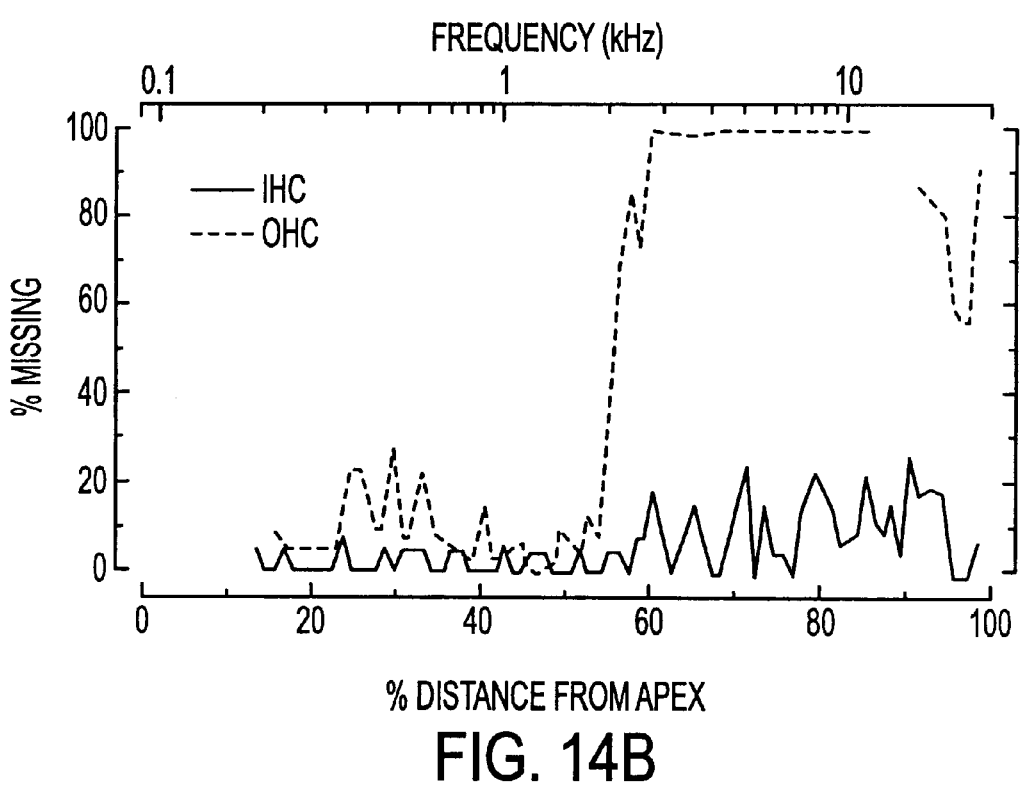

FIGS. 13A–D illustrate mean inner and outer hair cell counts in a cytocochleogram which portrays missing hair cell percentages on the Y axis as a function of the measured percent distance from the cochlear apex. The associated frequency region of the cochlea is plotted on the X-axis. FIGS. 14A and 14B depict individual cytocochleograms from a pretreated noise exposed cochlea, and a saline treated noise exposed cochlea, respectively. FIG. 13A demonstrates that there is very little inner or outer hair cell loss in control animals not exposed to noise. FIG. 13B shows that the six hrs 4 kHz octave band noise exposure caused substantial hair cell loss, with maximal loss occurring between 5 and 6 kHz. Sixty to 80% of the outer hair cells were lost in the region between 3 and 8 kHz on the cochlea. Fewer inner hair cells were lost (maximum of 30%) in approximately the same region of the cochlea. In contrast, as shown in 4C, there was a substantial reduction in both outer and inner hair cell loss in the pre-treatment group compared to saline-noise (20 to 30% outer hair cell loss vs 60 to 80%, 0 to 10% inner hair cell loss versus 20 to 30%, respectively). The outer hair cell loss reached statistical significance for pre-treatment vs saline saline-noise groups (p<0.05) but not for inner hair cell differences. As noted, in FIG. 13D, there was no statistically significant difference in hair cell loss in the post-treatment group compared saline-noise group.

3.3. Cytocochleogram—Area Under the Curve Analysis

A multi-way ANOVA was applied to demonstrate that there were no ear-to-ear differences among all animals. Therefore, each cochlea was used in the area under the curve analysis as independent observations giving 10 observations across three treatment groups (total of 30 observations).

Using a Kruskal-Wallis analysis, it was demonstrated that there was a significant treatment effect for both the inner hair cell (JHC) and outer hair cell (OHC) area under the curve measures. For IHC and OHC areas the Chi-squared values were 6.057 (df=2) and 11.760 (df=2), respectively. Dunn's multiple comparison tests determined that pre-treatment with anti-oxidants provided the greatest protection for auditory hair cells showing the least area under the curve for the OHC measures. Pre-treatment OHC values were significantly different from both the saline and post-treatment groups. However, for IHC measures, the pre-treatment of anti-oxidants was not significantly different from the saline group, but was significantly different from the post-treatment group.

4. Discussion

While transducing acoustical energy into neural signals, the cochlea produces ROS as a normal cellular byproduct. Under normal circumstances, various antioxidant defense mechanisms present in the inner ear prevent these damaging radicals from causing any permanent harm (Kopke et al., A radical demise: toxins and trauma share common pathways in hair cell death. In Ototoxicity: Basic Sciences and Clinical Applications. (Eds. D. Henderson, R. Salvi, A. Quaranta, S. McFadden, and R. Buckard) *Annals of the New York Academy of Sciences*, Volume 884, New York, N.Y. (1999)). With extreme acoustic over-stimulation, normal homeostasis is no longer maintained however, and cells may undergo a non-recoverable injury leading to a permanent noise induced hearing loss. By augmenting the native antioxidant defense system during periods surrounding a noise stress, our results suggest that permanent threshold shift of hearing may be prevented or reduced.

The present study demonstrates the potential efficacy of a combination of two Food and Drug Administration approved agents in preventing, and to a lesser extent, reversing permanent noise-induced threshold shifts in a chinchilla model of NIHL. The thresholds reported in this study were similar to data published from other labs, which utilized the same animal model for NIHL (Hu et al., *Hear Res,* 113, 198–206 (1997); Henderson et al., 1973). After an intense six-hour noise exposure, we found very substantial hair cell loss as well as significant permanent shifts in evoked inferior colliculus auditory thresholds. Threshold shifts and hair cell losses reported in this study were more substantial than in a previous experiments (Hu et al., *Hear Res,* 113, 198–206 (1997)) which utilized a 4-hr exposure of the same frequency spectrum and intensity of sound. By increasing the noise trauma we increased the difference in threshold shift between untreated (saline-noise) and treated subjects.

Despite the intensity of this noise exposure, the antioxidant combination, when applied shortly before the noise exposure reduced permanent threshold shifts by 75%, and inner and outer hair cell loss by over 50%. These data are consistent with previous studies using other antioxidant compounds or compounds with antioxidant actions, administered either systemically (Seidman et al., *Otolaryngol Head Neck Surg,* 109, 1052–6 (1993); Attias et al., *Am J Otolaryngol,* 15, 26–32 (1994); Quirk et al., *Hear Res,* 74,217–20(1994); Yamasoba et al., *Twenty-first Midwinter Research Meeting of the Association for Research in Otolaryngology* Association for Research in Otolaryngology, St. Petersburg Beach, Fla., pp. 133, abstract 531 (1998); Yamasoba, *Brain Res,* 784, 82–90(1998); Komjathy et al., *Midwinter Meeting of the Association for Research in Otolaryngology,* Vol. Abstract 748 St. Petersburg Beach, Fla. (1998)), or applied to the round window membrane (Hu et al., *Hear Res,* 113, 198–206 (1997); Shoji et al. *Twenty-first Midwinter Research Meeting of the Association for Research in Otolaryngology* (Ed, R., P. G.) Association for Research in Otolaryngology, St. Petersburg Beach, Fla., pp. 135, abstract 539, (1998); Keithley, et al. *Twenty-first Midwinter Research Meeting of the Association for Research in Otolaryngology* (Ed, R., P. G.) Association for Research in Otolaryngology, St. Petersburg Beach, Fla., pp. 136, abstract 540 (1998); Liu et al., *Midwinter Meeting of the Association for Research in Otolaryngology,* Vol. 22, Abstract 604, St. Petersburg Beach, Fla. (1999); Hight et al., supra) prior to noise exposure. Administration of the antioxidant agents utilized in this study resulted in a reduction in threshold shift and/or hair cell loss and further support the hypothesis that ROS play a significant role in the causative mechanisms of NIHL. The pharmacological agents used in this study, when compared to other published agents (described above), may prove suitable in future clinical trials to prevent NIHL. The ability to use an oral agent would by inference be useful for groups exposed to periodic noise trauma at known intervals. Whether or not these agents are protective for impulse noise is not known.

Administration of the antioxidant compounds after noise exposure significantly reduced permanent threshold shift but evidenced no effect in preventing hair cell loss in our model. Improvement of hearing thresholds in the post-treatment group despite hair cell losses, which were equivalent to untreated saline-noise group, is unclear. There could have been an enhancement of cellular repair processes or prevention of on-going sub-lethal damage in the surviving hair cells, which could not be detected with our histological techniques, our procedure identified only viable hair cells. Thus, the enhanced cochlear function in the post-treatment group may have been a result of enhanced function in the remaining hair cells (i.e. compared to saline-noise controls). The relative lack of effectiveness when the antioxidants were given after the noise is not clear, but the duration and intensity of the noise exposure may have exceeded the agent's antioxidant capacity when given after the noise exposure. Consequently, the noise-induced burst of ROS may have initiated a precipitation of excitotoxicity similarly observed after CNS trauma or ischemia (Mattson and Scheff, *J Neurotrauma,* 11, 3–33 (1994)), or it may have activated self-propagating chain reactions of lipid peroxidation or other oxidation cascades which were not effectively countered by our antioxidant combination (Mattson and Scheff, supra).

It has been previously reported that loss of hair cells of the organ of Corti is not the only characteristic of hearing loss. The degree of hair cell loss following noise trauma is sometimes difficult to correlate with the auditory threshold shift (Latayc and Campo, *J Acoust Soc Am,* 99(3), 1621–1632 (1995); Liberman and Beil, *Acta Otolarnygol.* 88, 161–176 (1979) and Ades et al., *Acta Otolaryngol* 78, 192–206 (1974)) and with the total dose of noise (Erlandsson et al. *Acta Otolarnygol.* (Stockholm) 103, 204–211 (1987)). It has been reported that the orderliness of the stereocilia, along with cellular changes such as swelling of the synapses at the base of outer and innerhaircells (Spoendlin, *Acta Otolarnygol.* 71, 166–176(1979); Robertson, *Hear. Res.* 9,263–278 (1983); Canlon et al., Physiologic and morphologic aspects to low-level acoustic stimulation (1992) In *Noise Induced Hearing Loss*: Eds. Dancer, A., Henderson, D., Salvi, R., and Hamemik, R. P. 489–499 (1992)), are as important as the absence of hair cells (Ulfendahl et al., *Eur J Neurosci* 5, 713–723 (1993)). In the present study, we too report this imperfect correlation of hair cell loss with hearing loss. As reported previously, we agree that two distinct mechanisms of acoustic trauma may take place within the organ of Corti, i.e. metabolic and mechanical damage (Lataye and Campo, supra, Ades et al., supra). While simple hair cell loss is easily observed, at what point do degenerative changes render a hair cell non-functional, partially or intermittently functional? And of equal importance how does this correlate with auditory threshold measurements?

Alternatively, the burst of ROS may initiate necrosis and/or apoptosis (programmed cell death) pathways (Raffray and Cohen, *Pharmacol Ther,* 75, 153–77 (1997); Liu et al., Inhibition of ICE protects auditory sensory cells from cisplatin-induced apoptosis., *Twenty-first Midwinter Research Meeting of the Association for Research in Otolaryngology* Association for Research in Otolaryngology, St. Petersburg Beach, Fla. (1998); Nakagawa et al., *ORL J Otorhinolaryngol Relat Spec,* 59,303–10(1997)) that could not be prevented or terminated by these compounds given under these conditions. A recent study by Pirvola et al., *J Neurosci,* 20(1), 43–50 (2000) demonstrated DNA fragments of hair cell nuclei after ototoxic drug and noise exposure in vitro and in vivo. Pirvola and colleagues report that the c-Jun-N-terminal kinase (INK) pathway, which is associated with apoptosis is activated in hair cells after noise exposure.

On-going hair cell loss leading to transient gaps in the reticular lamina, with exposure of hair cells to toxic endolymph, might play a role in propagation of the injury after noise cessation (Fredelius, *Acta Otolaryngol (Stockh),* 106, 373–385 (1988)). This catabolic time course may not be amenable to antioxidant reversal.

A As with other biological systems, a concentration effect of toxin (in this case toxic noise) may produce zones of necrosis in areas of maximal concentration surrounded by zones of injury where the concentration is reduced. The injured cells may be repaired or undergo programmed cell death depending on the severity of the injury and availability of agents which might induce repair (Raffray and Cohen, supra). Further study is needed to optimize the conditions and agents that may reverse hearing loss when the agents are administered after noise exposure. Although further preclinical study is warranted, these data suggest that it may be feasible to augment mechanical hearing protection with pharmacological antioxidant agents to more completely prevent permanent hearing loss due to excessive noise.

REFERENCES

1. Ohlin, D. U.S. Army Center for Health Promotion and Preventative Medicine, (personal communication)
2. Ohlin, D. Hearing Conservation Special Study No.51–01-PM82–93, 15 Years Revisited: The Prevalence of Hearing Loss Among Selected U.S. Army Branches, 1992
3. Price G., Kalb J., Garinther G., Toward A Measure of Auditory Handicap In The Army. Ann. Otol. Rhinol. Laryngol. 1989; 98: 42–52
4. Center for Disease Control. Leading work related diseases and injuries-United States MMWR. 1983;32:24–6, 32
5. Hu B., Zheng X., McFadden S., Kopke R., Henderson D., R-PIA attenuates noise-induced hearing loss in the chinchilla. Hear. Res. 1997; in press
6. Clerici W., Hensley K., DiMartino D., Butterfield D., Direct detection of ototoxicant-induced reactive oxygen species generation in cochlear explants. Hear. Res. 1996;98:116–124
7. Kopke R., Liu., Gabaizadeh R., Jacono A., Feghali J., Spray D., Garcia P., Steinman H., Malgrange B., Ruben R., Rybak L., Van De Water T., The use of organotypic cultures of Corti's organ to study the protective effects of antioxidant molecules on cisplatin induced damage of auditory hair cells. Am. J. Otol. 1997; in press
8. Clerici W., Zhang L., Yang, L., Parasad M., Spin trap protection against fluid percussion traumatic brain injury-induced auditory dysfunction Abstracts of the 20th ARO Midwinter Meeting. St. Petersburg, Fla. 1997 (Abstract 451)
9. Ravi R., Somani S., Rybak L., Mechanism of cisplatin ototoxicity: antioxidant system. Pharmacol. Toxicol. 1995;76:386–394
10. Bellomo G., Orrbenius S., Altered thiol and calcium homeostasis in oxidative hepatocellular injury. Hepatology 1985;5:876–82
11. Ratan R., Murphy T., Baraban. Macromolecular synthesis inhibitors prevent oxidative stress-induced apoptosis in embryonic cortical neurons by shunting cysteine from protein synthesis to glutathione. J. Neurosci. 1994; 14(7):4385–4392
12. Quirk W., Seidman M., Cochlear vascular changes in response to loud noise. Am. J. Otol. 1995;16:322–325
13. Landi L., Pasquali P., Cabrini L., Effect of oxygen free radicals on ubiquinone in aqueous solution and phospholipid vesicles. Biochim. Biophys. Acta. 1987;902:200–206
14. Mulroy M., Henry W., Exposure to loud noise induces temporary microlesions in the plasma membranes of cochlear hair cells. Abstracts of the 20th ARO Midwinter Meeting. St. Petersburg, Fla. 1997 (Abstract 814).
15. Ernfors P., Canlon B., Aminoglycoside excitement silences hearing. Nature Med. 1996;2(12):1313–14
16. Jacono A., Kopke R., Vugmeyster L., et al Changes in cochlear antioxidant enzyme levels after conditioning noise exposure in the chinchilla. Abstracts of the 19th ARO Midwinter Meeting. St Petersburg, Fla. 1996 (Abstract 132).
17. Yamane H., Nakai Y., Takayama M., Konishi K., Iguchi H., Nakagawa T., Shibata S., Kato A., Sunami K., Kawakatsu C., The emergence of free radicals after acoustic trauma and strial blood flow. Acta Otolaryngol. Suppl (Stockholm). 1995;519:87–92
18. Liu A., Experimental study on the mechanism of free radical in blast trauma induced hearing loss. Chinese J. Otorhinolaryngol. 1992;27:24–26
19. Bobbin R., Fallon M., LeBlanc C., Baber A., Evidence that glutathione is the unidentified amine (Unk 2.5) released by high potassium into cochlear fluids. Hear. Res. 1995;87:49–54
20. Yamasoba T., Nuttall A., Miller J., The role of glutathione in protection against noise-induced hearing loss. Poster 32, 1997 Annual Meeting AAOHNS, San Francisco Calif.
21. Quirk W., Shivapuja B., Schwimmer C., Seidman., Lipid peroxidation inhibitor attenuates noise-induced temporary threshold shifts. Hear. Res. 1994;74:217–20
22. Seidman M., Shivapuja B., Quirk W., The protective effects of allopurinol and superoxide dismutase on noise-induced cochlear damage. Otollaryngol Head Neck Surg 1993; 109:1052–56
23. Meister A., Glutathione deficiency produced by inhibition of its synthesis, and its reversal: applications in research and therapy. Pharmacol Ther, 1991;51:155–94
24. Miller L., Hsu C., Therapeutic potential for adenosine receptor activation in ischemic brain injury. J., of Neurotrama. 1992;9:S563-S577
25. Fessenden J., Coling D., Schacht J., Detection and characterization of nitric oxide synthase in the mammalian cochlea. Brain Res. 1994;668:9–15
26. Rudolphi K., Schubert P., Parkinson F., Fredholm B., Neuroprotective role of adenosine in cerebral ischaemia. Trends Pharamacol Sci. 1992; 13:439–445
27. Basile A., Huang J., Xie C., Webster D., Berlin C., Skolnick P. N-methyl-D-aspartate antagonosts limit aminoglycoside antibiotic-induced hearing loss. Nature Medicine 1996; 2(12); 1338–1343
28. Balough B J, Hoffer M E, Wester D, and O'Leary M J: Destructive ototoxic medicines: The kinetics of gentamicin uptake in the inner ear of Chinchilla Laniger following middle ear administration in a sustained release vehicle, In Press Otoalryngol Head Neck Surgery
29. Hoffer M E, Balough B, Wester D, Kopke R D, and O'Leary M J: Destructive ototoxic medicines: "Finding the therapeutic window into the inner ear" in Endolymphatic Sac Surgery, Arenberg I and Graham M (eds). Singular Publishing, 1998 (in press)
30. Gruber H E, Hoffer M E, McAllister D R, Laikind P K, Lane T, Schmid-Schoenbein G, Engler R L: Increased Adenosine Concentration in Blood from Ischemic Myocardium by AICA Riboside: Effects on Flow, Granulocytes, and Injury. Circulation, 80(5): 1400–1411, 1989.
31. Mullane K. Acadesine: the prototype adenosine regulating agent for reducing myocardial ischaemic injury. Cardiovascular Research. 1993;27: 43–47
32. Hooper D., Bagasra O., Marini J., Zborek A. et al. Prevention of experimental allergic encephalomyelitis by targeting nitric oxide and peroxynitrite: implications for the treatment of multiple sclerosis. Proc. Natl Acad Sci USA, 94(6):2528–2533, 1997.

Obviously, many modifications and variations of the present invention are possible in light of the above teachings. It is therefore to be understood that, within the scope of the appended claims, the invention may be practiced otherwise than as specifically described.

What is claimed is:

1. A method for preventing and treating noise or toxin induced sensorineural hearing loss, comprising:

(a) selecting subjects experiencing said hearing loss or at risk for acute exposure to noise, toxins, or other stressors causing said hearing loss; and (b) administering to said subjects a pharmaceutically effective amount of a compound selected from the group consisting of:
   steroids;
   compounds that are transported into inner ear hair cells and then synthesized by said cells into glurathione; and
   combinations thereof.

2. The method of claim 1 wherein the compound is administered systemically.

3. The method of claim 2 wherein the compound is administered orally.

4. The method of claim 1 wherein the compound is administered topically.

5. The method of claim 4 wherein the compound is administered topically through a catheter to the round window membrane of the inner ear.

6. A method for preventing and treating sensorineural hearing lass, comprising:
   (c) selecting subjects experiencing said hearing loss or at risk for acute exposure to noise, toxins, or other stressors causing said hearing loss; and
   (d) administering to said subjects a pharmaceutically effective amount of a mixture of compounds selected from the group consisting of:
      N-L-acetylcysteine;
      an ester of salicylic acid;
      a salt of salicylic acid; and
      any combination thereof.

7. A method for preventing and treating non-presbycusis related hearing loss, comprising:
   (a) selecting subjects experiencing said hearing loss or at risk for acute exposure to noise, toxins, or other stressors causing said hearing loss; and
   (b) administering to said subjects a pharmaceutically effective amount of aectyl-L-carnitine.

8. The method of claim 7, wherein said pharmaceutically effective amount of acetyl-L-carnitine is administered as a mixture including N-L-acetylcysteine.

* * * * *